US012740979B2

(12) United States Patent
Calvayrac et al.

(10) Patent No.: US 12,740,979 B2
(45) Date of Patent: Sep. 22, 2026

(54) METHODS FOR THE TREATMENT OF CANCERS THAT HAVE ACQUIRED RESISTANCE TO KINASE INHIBITORS

(71) Applicants: INSERM (INSTITUT NATIONAL DE LA SANTÉ ET DE LA RECHERCHE MÉDICALE), Paris (FR); UNIVERSITÉ TOULOUSE, III—PAUL SABATIER, Toulouse (FR); INSTITUT CLAUDIUS REGAUD, Toulouse (FR)

(72) Inventors: Olivier Calvayrac, Toulouse (FR); Gilles Favre, Toulouse (FR); Sarah Figarol, Toulouse (FR)

(73) Assignees: INSERM (INSTITUT NATIONAL DE LA SANTÉ ET DE LA RECHERCHE MÉDICALE), Paris (FR); UNIVERSITÉ TOULOUSE, III—PAUL SABATIER, Toulouse (FR); INSTITUT CLAUDIUS REGAUD, Toulouse (FR)

(*) Notice: Subject to any disclaimer, the term of this patent is extended or adjusted under 35 U.S.C. 154(b) by 926 days.

(21) Appl. No.: 17/774,997

(22) PCT Filed: Nov. 6, 2020

(86) PCT No.: PCT/EP2020/081309

§ 371 (c)(1),
(2) Date: May 6, 2022

(87) PCT Pub. No.: WO2021/089791

PCT Pub. Date: May 14, 2021

(65) Prior Publication Data

US 2022/0401436 A1 Dec. 22, 2022

(30) Foreign Application Priority Data

Nov. 8, 2019 (EP) .................................... 19208154

(51) Int. Cl.
*A61K 31/4709* (2006.01)
*A61K 31/437* (2006.01)
(Continued)

(52) U.S. Cl.
CPC ........ *A61K 31/4709* (2013.01); *A61K 31/437* (2013.01); *A61K 31/506* (2013.01);
(Continued)

(58) Field of Classification Search
CPC .............. A61K 31/4709; A61K 31/437; A61K 31/506; A61K 31/517; A61K 31/5377;
(Continued)

(56) References Cited

U.S. PATENT DOCUMENTS 11,124,839 B2 * 9/2021 Gualberto .............. A61K 31/00

FOREIGN PATENT DOCUMENTS

| | | | | |
|---|---|---|---|---|
| WO | 2006135636 A2 | | 12/2006 | |
| WO | WO-2018085518 A2 | * | 5/2018 | ............. A61K 31/00 |
| WO | WO-2020092517 A1 | * | 5/2020 | ........... A61K 31/404 |

OTHER PUBLICATIONS

Cortes Phase 1 Study of Tipifarnib in Combination WithImatinib for Patients With Chronic MyelogenousLeukemia in Chronic Phase After Imatinib Failureâ Cancer 2007 110 9 1877-2118 (Year: 2007).*

(Continued)

*Primary Examiner* — Robert B Mondesi
(74) *Attorney, Agent, or Firm* — WCF IP

(57) ABSTRACT

Resistance to kinase inhibitors exemplifies the greatest hindrance to effective treatment of cancer patients. Recent studies have suggested that the onset of said resistance might not only be explained by a drug selection of pre-existing resistant sub-clones as it what was generally assumed, but may also arise de novo from a small population of drug-tolerant cells (DTC) that initially resists the treatment by (Continued)

Figures 1A, 1B:
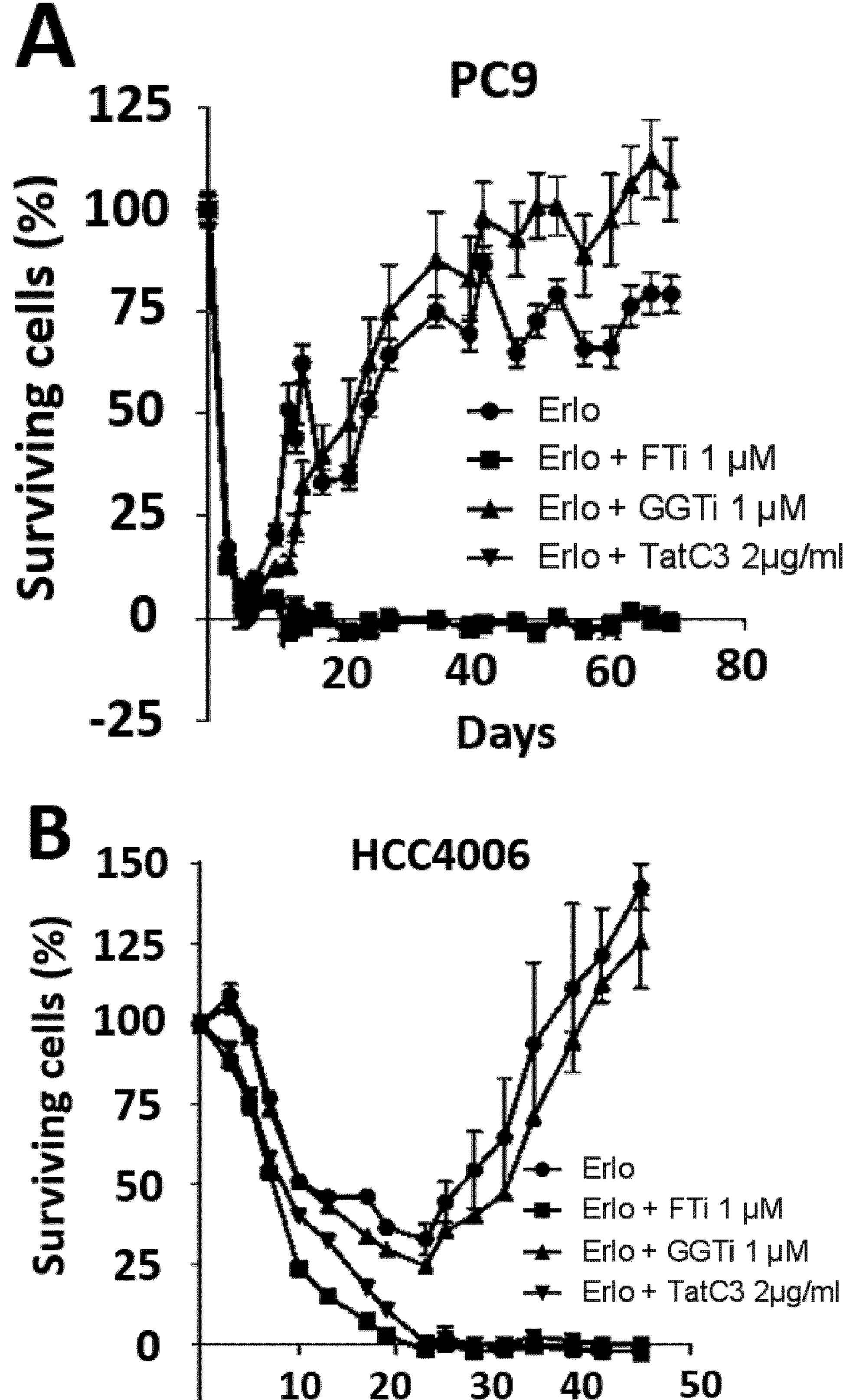

entering a slow cycling state. Thus, targeting these DTC should be a new promising approach to hamper the emergence of secondary resistance to kinase inhibitors. The inventors now demonstrate that farnesyltransferase (but not geranylgeranyl transferase) inhibition can prevent the emergence of said resistance in different oncogenic contexts. In particular, the inventors determined invitro the efficacy of farnesyltransferase inhibitor (i.e. Tipifarnib) in combination with erlotinib in several EGFR-mutated cell lines. They showed that the combination efficiently eliminated all drug tolerant cells, and fully prevented the emergence of resistant clones. Interestingly, similar results were observed in other oncogenic models such as ALK-translocated lung cancer cells or BRAF-mutated melanoma cells. Thus the present invention relates to use of farnesyl transferase inhibitors for the treatment of cancers that have acquired resistance to kinase inhibitors.

11 Claims, 8 Drawing Sheets

(51) Int. Cl.

| | |
|---|---|
| ***A61K 31/506*** | (2006.01) |
| ***A61K 31/517*** | (2006.01) |
| ***A61K 31/5377*** | (2006.01) |
| ***A61P 11/00*** | (2006.01) |
| ***A61P 35/00*** | (2006.01) |

(52) U.S. Cl.
CPC ........ *A61K 31/517* (2013.01); *A61K 31/5377* (2013.01); *A61P 11/00* (2018.01); *A61P 35/00* (2018.01)

(58) Field of Classification Search
CPC ............ A61K 31/4184; A61K 31/4545; A61K 31/4706; A61K 31/496; A61K 31/4985; A61K 31/519; A61K 31/675; A61K 31/55; A61P 35/00
USPC ...................................................... 514/235.5
See application file for complete search history.

(56) References Cited

OTHER PUBLICATIONS

Chan Transl Lung Cancer Res 2015 (Year: 2015).*
Seshacharyulu Expert Opinion on Therapeutic Targets 2012 (Year: 2012).*
Spicer International Journal of Clinical Practice 2005 (Year: 2005).*
Yuan Signal Transduction and Targeted Therapy 2019 (Year: 2019).*
Bishayee "A broad-spectrum integrative design for cancer prevention and therapy: The challenge ahead" Seminars in Cancer Biology 2015 35 S1-S4 (Year: 2015).*
Upadhyay "Cancer An unknown territory; rethinking before going ahead" Genes & Diseases 2021 8 655-661 (Year: 2021).*
Cortes Cancer 2007 110 9 2000-2005 (Year: 2007).*
Hartmann Curr Drug Metab 2009 (Year: 2009).*
Iqbal Chemotherapy Research and Practice 2014 (Year: 2014).*
Wheeler Nature Reviews 2010 (Year: 2010).*
Russell R Hoover et al, "Overcoming STI571 resistance with the farnesyl transferase inhibitor SCH66336", Blood, vol. 100, No. 3, Aug. 1, 2002 (Aug. 1, 2002), p. 1068-1071.
Gotlib J et al, "Abstract 3384: Tipifarnib (Zarnestra) and imatinib (Gleevec) combination therapy in patients with advanced chronic myelogenous leukemia (CML): preliminary results of a phase I study", Blood, the American Society of Hematology, US, vol. 102, Jan. 1, 2003 (Jan. 1, 2003), p. 909-910.
Giovanni Martinelli et al, "Farnesyltransferase Inhibition in Hematologic Malignancies: The Clinical Experience With Tipifarnib", Clin Adv Hematol Oncol,, vol. 6, May 1, 2008 (May 1, 2008), p. 303-310.

* cited by examiner

METHODS FOR THE TREATMENT OF CANCERS THAT HAVE ACQUIRED RESISTANCE TO KINASE INHIBITORS

CROSS-REFERENCE TO RELATED APPLICATIONS

This application is a Rule 371 filing from PCT/EP2020/081309 filed Nov. 6, 2020, which claimed priority to European Application 19208154.5 filed Nov. 8, 2019.

FIELD OF THE INVENTION

The present invention is in the field of medicine, in particular oncology.

BACKGROUND OF THE INVENTION

Lung cancer is the leading cause of cancer deaths worldwide[1]. Metastatic non-small-cell lung cancer (NSCLC) has recently benefited from two consecutive breakthroughs: the identification of oncogene drivers, such as EGFR mutations, leading to the development of targeted therapies, and the understanding of the cancer immunity cycle leading to the development of immune checkpoint inhibitors.

First-generation EGFR-Tyrosine Kinase Inhibitors (EGFR-TKI) such as Erlotinib or Gefitinib are effective therapies for NSCLC bearing EGFR-activating mutations[2]. However, despite 70% response rate, patients usually relapse with a median time of 12 months due to the development of drug resistance. The mechanisms of acquired resistance include the $EGFR^{T790M}$ mutation, the activation of bypass pathway including MET[3] or HER2[4], the epithelial to mesenchymal transition (EMT)[5], and the transformation into small cell lung cancer[6], among others[7]. These resistances can be also mediated by the reactivation of proliferation/survival pathways downstream from EGFR, mainly PI3K/AKT, MEK/ERK or STAT[8,9]. Initially, it was thought that targeting the additional genetic alterations found in the tumor at the time of relapse could solve the problem of resistance. However, inter- and intra-tumoral mutational heterogeneity has invalidated this strategy. Indeed, patients treated with third-generation EGFR-TKI Osimertinib, which efficiently targets the T790M gatekeeper mutation, also relapse due to the emergence of new resistance mechanisms (e.g. EGFR-C797S/G mutation)[10].

Recent in vitro studies have suggested that the onset of EGFR-TKI resistance might not only be explained by a drug selection of pre-existing resistant sub-clones as it what was generally assumed, but may also arise de novo from a small population of drug-tolerant cells (DTC) that initially resists the treatment by entering a slow cycling state[11]. Over time, some of these cells can re-enter cell cycle and eventually acquire genetic alterations that allow them to fully recover proliferative capacities[12,13]. DTCs have been described essentially in the EGFR-mutated PC9 lung cell line, which reproduces in vitro the main stages displayed in patients: i) a strong initial response during the first 5 days of treatment with 1 μM EGFR-TKI (a dose 50 to 100 times the IC50 of this cell line and corresponding to the blood concentration in patients) resulting in the mortality of a vast majority of cells; ii) a period of latency of several days/weeks is then observed, which corresponds to the presence of remaining DTCs. These cells have been described as low proliferative cells that express cancer stem cell markers as CD133 or CD24 and have undergone an epigenetic reprogramming without genotype alteration[11,14]; iii) after several weeks of treatment, some of these cells can acquire de novo genetic modifications such as the $EGFR^{T790M}$ resistance mutation (in the case of first-generation EGFR-TKI treatment) or other genetic alterations[12,13].

Other studies have shown the existence of a similar cell state, also referred to as Minimal Residual Disease (MRD) generated in response to several anti-cancer therapies in NSCLC but also in other cancers such as metastatic melanoma[15], glioblastoma[16] or acute myeloid leukemia[17]. Nevertheless, this particular state remains very poorly characterized, and we still don't know by which molecular mechanism(s) tumor cells evolve towards a DTC state, how these DTC generate resistance mutations, and to which extend these cells can promote resistance in patients. Thus, targeting these DTC should be a new promising approach to hamper the emergence of secondary resistance to EGFR-TKI. However, we still lack an accurate in vivo phenotypic and molecular characterization of this particular state, which is a prerequisite to the development of new therapeutics.

SUMMARY OF THE INVENTION

As defined by the claims, the present invention relates to methods, pharmaceutical compositions and kits for the treatment of cancers that has acquired resistance to kinase inhibitors.

DETAILED DESCRIPTION OF THE INVENTION

The first object of the present invention relates to a method of treating cancer in a subject in need thereof comprising administering to the subject a therapeutically effective combination comprising a kinase inhibitor and a farnesyltransferase inhibitor.

A further object of the present invention relates to a method delaying and/or preventing development of a cancer resistant to a kinase inhibitor in a subject comprising administering to the subject a therapeutically effective amount of the kinase inhibitor in combination with a farnesyltransferase inhibitor.

As used herein the term "resistance to kinase inhibitors" is used in its broadest context to refer to the reduced effectiveness of at least one kinase inhibitor to inhibit the growth of a cell, kill a cell or inhibit one or more cellular functions, and to the ability of a cell to survive exposure to an agent designed to inhibit the growth of the cell, kill the cell or inhibit one or more cellular functions. The resistance displayed by a cell may be acquired, for example by prior exposure to the agent, or may be inherent or innate. The resistance displayed by a cell may be complete in that the agent is rendered completely ineffective against the cell, or may be partial in that the effectiveness of the agent is reduced. Accordingly, the term "resistant" refers to the repeated outbreak of cancer, or a progression of cancer independently of whether the disease was cured before said outbreak or progression.

A further object of the present invention relates to a method of treating a cancer resistant to a kinase inhibitor in a subject in need thereof comprising administering to the subject a therapeutically effective amount of a famesyltransferase inhibitor.

A further object of the present invention relates to a method of preventing resistance to an administered kinase inhibitor in a subject suffering from a cancer comprising administering to the subject a therapeutically effective amount of a farnesyltransferase inhibitor.

A further object of the present invention relates to a method for enhancing the potency of a kinase inhibitor administered to a subject suffering from a cancer as part of a treatment regimen, the method comprising administering to the subject a pharmaceutically effective amount of a farnesyltransferase inhibitor in combination with the kinase inhibitor.

A further object of the present invention relates to the use of a famesyltransferase inhibitor for inhibiting or preventing proliferation of cancer persister cell or formation of colonies of cancer persister cell, thereby preventing or delaying the cancer relapse and/and the emergence of acquired resistance to a therapies with kinase inhibitors. In addition, this effect against cancer persister cell may allow to reach a complete response to the cancer treatment. Indeed, the farnesyltransferase inhibitor would be able to eliminate the cancer persister cell. It also relates to a method for removing or decreasing the cancer persister cell population and/or for preventing or delaying the cancer relapse and/and the emergence of acquired resistance to a cancer treatment, comprising administering a therapeutically effective amount of a farnesyltransferase inhibitor, thereby removing or decreasing the cancer persister cell population. The famesyltransferase inhibitor would be beneficial in targeting viable "persister" tumor cells and thus may prevent the emergence of drug-resistant clone(s), in particular in the context of a combined treatment with a kinase inhibitor.

As used herein, the terms "persister cell", "persister cancer cell", "drug tolerant persister" and "DTP" are intended to refer to a small subpopulation of cancer cells that maintain viability under anti-cancer targeted therapy treatments, in particular a treatment with a kinase inhibitor. More particularly, it refers to cancer cells that have a tolerance to high concentrations of a treatment of a kinase inhibitor, when it is used in concentrations that are 100 of times higher than IC50. These cells have a slow growth and are almost quiescent. The famesyltransferase inhibitor of the present invention is thus particularly suitable for eradicating drug-tolerant expanded persister. As used herein, the term "drug-tolerant expanded persister", or "drug tolerant cells" as used herein, refers to cancer cells that are capable to proliferate with continuous cancer drug treatment in high concentrations, in particular a treatment with a kinase inhibitor.

As used herein, the term "relapse" refers to reappearance of the cancer after an initial period of responsiveness (e.g., complete response or partial response). The initial period of responsiveness may involve the level of cancer cells falling below a certain threshold, e.g., below 20%, 15%, 10%, 5%, 4%, 3%, 2%, or 1%. The reappearance may involve the level of cancer cells rising above a certain threshold, e.g., above 20%, 15%, 10%, 5%, 4%, 3%, 2%, or 1%. More generally, a response (e.g., complete response or partial response) can involve the absence of detectable MRD (minimal residual disease). In some embodiments, the initial period of responsiveness lasts at least 1, 2, 3, 4, 6, 8, 10, or 12 months; or at least 1, 2, 3, 4, or 5 years.

As used herein, the term "kinase inhibitor" refers to any compound that is currently known in the art or that will be identified in the future, and includes any chemical entity that, upon administration to a subject, results in inhibition a kinase pathway in the cancer cells of the subject. In some embodiments, the kinase inhibitor is a small organic molecule. Kinase inhibitors include but are not limited to low molecular weight inhibitors, antibodies or antibody fragments, antisense constructs, small inhibitory RNAs (i.e. RNA interference by dsRNA; RNAi), and ribozymes. The kinase inhibitor is typically a small organic molecule. The term excludes biological macromolecules (e.g.; proteins, nucleic acids, etc.). Preferred small organic molecules range in size up to 2000 Da, and most preferably up to about 1000 Da.

According to the present invention, the kinase inhibitor is a kinase inhibitor for treating cancer. In particular, the kinase can be a tyrosine kinase, a serine/threonine kinase or a kinase with dual specificity. In a particular aspect, the kinase inhibitor is known to be associated with an acquired resistance during the cancer treatment. In a very particular aspect, the kinase inhibitor is associated with the occurrence of persister cancer cells during a treatment of cancer with this kinase inhibitor.

In some embodiments, the kinase inhibitors may target any one of the following kinases: EGFR family, ALK, B-Raf, MEK, FGFR1, FGFR2, FGFR3, FGFR4, FLT3, IGF1R, c-Met, JAK family, PDGFR α and β, RET, AXL, c-KIT, TrkA, TrkB, TrkC, ROS1, BTK and Syk.

In some embodiments, the kinase inhibitor is an inhibitor targeting a receptor tyrosine kinase, especially one selected from the group consisting of EGFR family, ALK, FGFR1, FGFR2, FGFR3, FGFR4, c-Met, RET, IGF1R, PDGFR α and β, c-KIT, FLT3, AXL, TrkA, TrkB, TrkC, and ROS1.

In some embodiments, the kinase inhibitor is an inhibitor targeting a tyrosine kinase selected from the group consisting of EGFR, ALK, B-Raf, MEK, c-Met, JAK, PDGFR α and R, RET and BTK. For instance, a group of tyrosine kinases evolutionary and structurally related to ALK is RET, ROS1, AXL and Trk families kinases.

The EGFR kinase inhibitors are well-known. For instance, reviews are published disclosing such EGFR kinase inhibitors (Expert Opinion on Therapeutic Patents December 2002, Vol. 12, No. 12, Pages 1903-1907; Kane, Expert Opinion on Therapeutic Patents February 2006, Vol. 16, No. 2, Pages 147-164; Traxler, Expert Opinion on Therapeutic Patents December 1998, Vol. 8, No. 12, Pages 1599-1625; Singh et al, Mini Rev Med Chem. 2016; 16(14): 1134-66; Cheng et al, Curr Med Chem. 2016; 23(29):3343-3359; Milik et al, Eur J Med Chem. 2017 Dec. 15; 142: 131-151; Murtuza et al, Cancer Res. 2019 Feb. 15; 79(4): 689-698; Tan et al, Onco Targets Ther. 2019 Jan. 18; 12:635-645; Roskoski, Pharmacol Res. 2019 January; 139: 395-411; Mountzios, Ann Transl Med. 2018 April; 6(8):140; Tan et al, Mol Cancer. 2018 Feb. 19; 17(1):29), the disclosure of which being incorporated herein by reference. Patent applications also disclose EGFR kinase inhibitors, for instance and non-exhaustively WO19010295, WO19034075, WO18129645, WO18108064, WO18050052, WO18121758, WO18218963, WO17114383, WO17049992, WO17008761, WO17015363, WO17016463, WO17117680, WO17205459, WO16112847, WO16054987, WO16070816, WO16079763, WO16125186, WO16123706, WO16050165, WO15081822, WO12167415, WO13138495, WO10129053, WO10076764, WO09143389, WO05065687, WO05018677, WO05027972, WO04011461, WO0134574, the disclosure of which being incorporated herein by reference. Specific examples of EGFR kinase inhibitors are disclosed in the following table.

The ALK kinase inhibitors are well-known. For instance, reviews are published disclosing such ALK kinase inhibitors (Beardslee et al, J Adv Pract Oncol. 2018 January-February; 9(1):94-101; Pacenta et al, Drug Des Devel Ther. 2018 Oct. 23; 12:3549-3561; Spagnuolo et al, Expert Opin Emerg Drugs. 2018 September; 23(3):231-241; Peters et al, Curr Treat Options Oncol. 2018 May 28; 19(7):37; Goldings et al, Mol Cancer. 2018 Feb. 19; 17(1):52; Karachaliou et al, Expert Opin Investig Drugs. 2017 June; 26(6):713-722; Liu et al, Curr Med Chem. 2017; 24(6):590-613; Crescenzo et al, Curr Opin Pharmacol. 2015 August; 23:39-44; Sgambato et al, Expert Rev Anticancer Ther. 2018 January; 18(1):71-80; Michellys et al, Bioorg Med Chem Lett. 2016 Feb. 1; 26(3):1090-1096; Straughan et al, Curr Drug Targets. 2016; 17(6):739-45), the disclosure of which being incorporated herein by reference. Patent applications also disclose ALK kinase inhibitors, for instance and non-exhaustively WO04080980, WO05016894, WO05009389, WO09117097, WO09143389, WO09132202, WO10085597, WO10143664, WO11138751, WO12037155, WO12017239, WO12023597, WO13013308, WO14193932, WO15031666, WO15127629, WO15180685, WO15194764, WO17076355, WO18001251, WO18044767, WO18094134, WO18127184, the disclosure of which being incorporated herein by reference. Specific examples of ALK kinase inhibitors are disclosed in the following table.

The B-Raf kinase inhibitors are well-known. For instance, reviews are published disclosing such B-Raf kinase inhibitors (Tsai et al, PNAS Feb. 26, 2008 105 (8) 3041-3046, Garnett et Marais, 2004 Cancer cell, Volume 6, Issue 4, Pages 313-319; Wilmott et al 2012, Cancer Therapy: Clinical, Volume 18, Issue 5; Fujimura et al, Expert Opin Investig Drugs. 2019 February; 28(2):143-148, Trojaniello et al, Expert Rev Clin Pharmacol. 2019 March; 12(3):259-266; Kakadia et al, Onco Targets Ther. 2018 Oct. 17; 11:7095-7107; Roskoski, Pharmacol Res. 2018 September; 135:239-258; Eroglu et al, Ther Adv Med Oncol. 2016 January; 8(1):48-56), the disclosure of which being incorporated herein by reference. Patent applications also disclose B-Raf kinase inhibitors, for instance and non-exhaustively WO14164648, WO14164648, WO14206343, WO13040515, WO11147764, WO11047238, WO11025968, WO11025951, WO11025938, WO11025965, WO11090738, WO09143389, WO09111280, WO09111279, WO09111278, WO09111277, WO08068507, WO08020203, WO07119055, WO07113558, WO07071963, WO07113557, WO06079791, WO06067446, WO06040568, WO06024836, WO06024834, WO06003378, WO05123696, the disclosure of which being incorporated herein by reference. Specific examples of B-Raf kinase inhibitors are disclosed in the following table.

The kinase inhibitors may target MEK (Mitogen-activated protein kinase kinase, also known as MAP2K, MP2K, MAPKK, MAPK/ERK kinase, JNK-activating kinase, c-Jun N-terminal kinase kinase (JNKK), Stress-activated protein kinase kinase (SAPKK); UniprotKB—Q02750 (MP2K1), P36507 (MP2K2), P46734 (MP2K3), P45985 (MP2K4), Q13163 (MP2K5), P52564 (MP2K6), 014733 (MP2K7)). Preferably, the kinase inhibitors target MEK-1 (also known as MAP2K1, MP2K1, MAPKK 1 or MKK1) and/or MEK-2 (also known as MAP2K2, MP2K2, MAPKK 2 or MKK2). Both MEK-1 and MEK-2 function specifically in the MAPK/ERK cascade. The MEK kinase inhibitors are well-known. For instance, reviews are published disclosing such MEK kinase inhibitors (Kakadia et al, Onco Targets Ther. 2018 Oct. 17; 11:7095-7107; Steeb et al, Eur J Cancer. 2018 November; 103:41-51; Sarkisian and Davar, Drug Des Devel Ther. 2018 Aug. 20; 12:2553-2565; Roskoski, Pharmacol Res. 2018 September; 135:239-258; Eroglu et al, Ther Adv Med Oncol. 2016 January; 8(1):48-56), the disclosure of which being incorporated herein by reference. Patent applications also disclose MEK kinase inhibitors, for instance and non-exhaustively WO15022662, WO15058589, WO14009319, WO14204263, WO13107283, WO13136249, WO13136254, WO12095505, WO12059041, WO11047238, WO11047055, WO11054828, WO10017051, WO10108652, WO10121646, WO10145197, WO09129246, WO09018238, WO09153554, WO09018233, WO09013462, WO09093008, WO08089459, WO07014011, WO07044515, WO07071951, WO07022529, WO07044084, WO07088345, WO07121481, WO07123936, WO06011466, WO06011466, WO06056427, WO06058752, WO06133417, WO05023251, WO05028426, WO05051906, WO05051300, WO05051301, WO05051302, WO05023759, WO04005284, WO03077855, WO03077914, WO02069960, WO0168619, WO0176570, WO0041994, WO0042022, WO0042003, WO0042002, WO0056706, WO0068201, WO9901426, the disclosure of which being incorporated herein by reference. Specific examples of MEK kinase inhibitors are disclosed in the following table.

The kinase inhibitors may target FGFR (Fibroblast growth factor receptor; UniprotKB—P11362 (FGFR1), P21802 (FGFR2), P22607 (FGFR3), P22455 (FGFR4)). The FGFR kinase inhibitors are well-known. For instance, reviews are published disclosing such FGFR kinase inhibitors (Katoh, Int J Mol Med. 2016 July; 38(1):3-15; Rizvi et Borad, J Gastrointest Oncol. 2016 October; 7(5):789-796; Tan et al, Onco Targets Ther. 2019 Jan. 18; 12:635-645, Shen et al, J Hematol Oncol. 2018 Sep. 19; 11(1):120; Porta et al, Crit Rev Oncol Hematol. 2017 May; 113:256-267; Cheng et al, Eur J Med Chem. 2017 Jan. 27; 126:476-490), the disclosure of which being incorporated herein by reference. Patent applications also disclose FGFR kinase inhibitors, for instance and non-exhaustively WO19034075, WO19034076, WO19001419, WO18028438, WO18049781, WO18121650, WO18153373, WO18010514, WO17028816, WO17070708, WO16091849, WO16134320, WO16054483, WO15059668, WO14007951, WO14026125, WO14129477, WO14162039, WO14172644, WO13108809, WO13129369, WO13144339, WO13179033, WO13053983, WO12008563, WO12008564, WO12047699, WO09153592, WO08078091, WO08075068, WO06112479, WO04056822, the disclosure of which being incorporated herein by reference. Specific examples of FGFR kinase inhibitors are disclosed in the following table. The FGFR kinase inhibitor can be selective one or several FGFR family members, especially members selected from FGFR1, FGFR2, FGFR3 and FGFR4.

The kinase inhibitors may target FLT3 (Receptor-type tyrosine-protein kinase FLT3, also known as FL cytokine receptor, Fetal liver kinase-2 (FLK-2), Fms-like tyrosine kinase 3 (FLT-3), Stem cell tyrosine kinase 1 (STK-1) or CD antigen: CD135; UniprotKB—P36888). The FLT3 kinase inhibitors are well-known. For instance, reviews are published disclosing such FLT3 kinase inhibitors (Stone, Best Pract Res Clin Haematol. 2018 December; 31(4):401-404; Wu et al, J Hematol Oncol. 2018 Dec. 4; 11(1):133; Short et al, Ther Adv Hematol. 2019 Feb. 15; 10:2040620719827310; Elshoury et al, Expert Rev Anticancer Ther. 2019 March; 19(3):273-286; Zhi et al, Eur J Med Chem. 2018 Jul. 15; 155:303-315; Tiong I S, Wei A H, Genes Chromosomes Cancer. 2019 Mar. 12, Gallogly et Lazarus, J Blood Med. 2016 Apr. 19; 7:73-83; Pitoia et Jerkovich, Drug Des Devel Ther. 2016 Mar. 11; 10:1119-

31), the disclosure of which being incorporated herein by reference. Patent applications also disclose XX kinase inhibitors, for instance and non-exhaustively WO19034538, WO17148440, WO15056683, WO13170671, WO13124869, WO13142382, WO13157540, WO11086085, WO09095399, WO09143389, WO08111441, WO08046802, WO06020145, WO06106437, WO06135719, the disclosure of which being incorporated herein by reference. Specific examples of FLT3 kinase inhibitors are disclosed in the following table.

The kinase inhibitors may target IGF1R (Insulin-like growth factor 1 receptor also known as Insulin-like growth factor I receptor (IGF-I receptor) or CD antigen: CD221; UniprotKB—P08069 or C9J5X1). The IGF1R kinase inhibitors are well-known. For instance, reviews are published disclosing such IGF1R kinase inhibitors (Qu et al, Oncotarget. 2017 Apr. 25; 8(17):29501-29518; Chen et al, Curr Top Med Chem. 2017 Nov. 20; 17(28):3099-3130), the disclosure of which being incorporated herein by reference. Patent applications also disclose IGF1R kinase inhibitors, for instance and non-exhaustively WO16082713, WO08076415, WO08000922, WO08076143, WO07121279, WO07083017, WO07075554, WO06080450, WO05095399, WO05097800, WO05037836, WO02092599, the disclosure of which being incorporated herein by reference. Specific examples of IGF1R kinase inhibitors are disclosed in the following table.

The kinase inhibitors may target c-Met (Hepatocyte growth factor receptor, also known as HGF/SF receptor, Proto-oncogene c-Met, Scatter factor receptor or Tyrosine-protein kinase Met; UniprotKB—P08581). The c-Met kinase inhibitors are well-known. For instance, reviews are published disclosing such c-Met kinase inhibitors (Zhang et al, Expert Opin Ther Pat. 2019 January; 29(1):25-41; Goździk-Spychalska et al, Curr Treat Options Oncol. 2014 December; 15(4):670-82; Bahrami et al, J Cell Physiol. 2017 October; 232(10):2657-2673; Zhang et al, Eur J Med Chem. 2016 Jan. 27; 108:495-504; Qi et al, World J Gastroenterol. 2015 May 14; 21(18):5445-53), the disclosure of which being incorporated herein by reference. Patent applications also disclose c-Met kinase inhibitors, for instance and non-exhaustively WO18153293, WO18187355, WO14000713, WO14032498, WO14067417, WO14180182, WO1307089, WO13107285, WO13149581, WO12006960, WO12015677, WO12034055, WO12048258, WO12075683, WO11039527, WO11079142, WO11121223, WO11143646, WO11149878, WO10007317, WO10007316, WO10007318, WO10019899, WO10059668, WO10089508, WO10089509, WO09143389, WO09143211, WO09056692, WO09093049, WO09068955, WO13013308, WO08023698, WO08008310, WO08102870, WO07036630, WO07066185, WO07023768, WO07002254, WO07002258, WO07111904, WO06104161, WO05082854, WO05082855, WO0160814 the disclosure of which being incorporated herein by reference. Specific examples of c-Met kinase inhibitors are disclosed in the following table.

The kinase inhibitors may target JAK (Tyrosine-protein kinase JAK2, also known as Janus kinase 2; UniprotKB—060674). The JAK kinase inhibitors are well-known. For instance, reviews are published disclosing such JAK kinase inhibitors (He et al, Expert Opin Ther Pat. 2019 February; 29(2):137-149; Hobbs et al, Hematol Oncol Clin North Am. 2017 August; 31(4):613-626; Senkevitch et Durum, Cytokine. 2017 October; 98:33-41; Leroy et Constantinescu, Leukemia. 2017 May; 31(5):1023-1038; Jin et al, Pathol Oncol Res. 2019 Jan. 31), the disclosure of which being incorporated herein by reference. Patent applications also disclose JAK kinase inhibitors, for instance and non-exhaustively WO19034153, WO18215389, WO18215390, WO18204238, WO17006968, WO17079205, WO17091544, WO17097224, WO17129116, WO17140254, WO17215630, WO16027195, WO16032209, WO16116025, WO16173484, WO16191524, WO16192563, WO15174376, WO15039612, WO14111037, WO14123167, WO14146492, WO14186706, WO13091539, WO13188184, WO11076419, WO10085597, WO10051549, WO10083283, WO10135621, WO10142752, WO10149769, WO11003065, WO09132202, WO09143389, WO09062258, WO09114512, WO09145856, WO09155565, WO09155551, WO08047831, WO08109943, WO08116139, WO08157207, WO07070514, WO07084557, WO07117494, WO07007919, WO06034116, WO06056399, WO06069080, WO05095400, WO04058753, WO04041789, WO04041814, WO04041810, WO03101989, WO0152892, the disclosure of which being incorporated herein by reference. Specific examples of JAK kinase inhibitors are disclosed in the following table.

The kinase inhibitors may target PDGFR (Platelet-derived growth factor receptor, also known as Platelet-derived growth factor receptor, CD140 antigen-like family member; UniprotKB—P16234 (PGFRA) P09619 (PGFRB)). The PDGFR kinase inhibitors are well-known. For instance, reviews are published disclosing such PDGFR kinase inhibitors (Roskoski, Pharmacol Res. 2018 March; 129:65-83; Andrick et Gandhi, Ann Pharmacother. 2017 December; 51(12):1090-1098; Khalique et Banerjee, Expert Opin Investig Drugs. 2017 September; 26(9):1073-1081; Miyamoto et al, Jpn J Clin Oncol. 2018 Jun. 1; 48(6):503-513; Gallogly et Lazarus, J Blood Med. 2016 Apr. 19; 7:73-83; Pitoia et Jerkovich, Drug Des Devel Ther. 2016 Mar. 11; 10:1119-31; Chen et Chen, Drug Des Devel Ther. 2015 Feb. 9; 9:773-9), the disclosure of which being incorporated herein by reference. Patent applications also disclose PDGFR kinase inhibitors, for instance and non-exhaustively WO11119894, WO08016192, WO07004749, WO03077892, WO03077892, WO0164200, WO0125238, WO0172711, WO0172758, WO9957117, and WO9928304, the disclosure of which being incorporated herein by reference. Specific examples of PDGFR kinase inhibitors are disclosed in the following table.

The kinase inhibitors may target RET (Proto-oncogene tyrosine-protein kinase receptor Ret, also known as Cadherin family member 12 or Proto-oncogene c-Ret; UniprotKB—P07949). The RET kinase inhibitors are well-known. For instance, reviews are published disclosing such RET kinase inhibitors (Roskoski et Sadeghi-Nejad, Pharmacol Res. 2018 February; 128:1-17; Zschabitz et GrWllich; Recent Results Cancer Res. 2018; 211:187-198; Grullich, Recent Results Cancer Res. 2018; 211:67-75; Pitoia et Jerkovich, Drug Des Devel Ther. 2016 Mar. 11; 10:1119-31), the disclosure of which being incorporated herein by reference. Patent applications also disclose RET kinase inhibitors, for instance and non-exhaustively WO18071454, WO18136663, WO18136661, WO18071447, WO18060714, WO18022761, WO18017983, WO17146116, WO17161269, WO17146116, WO17043550, WO17011776, WO17026718, WO14050781, WO07136103, WO06130673, the disclosure of which being incorporated herein by reference. Specific examples of RET kinase inhibitors are disclosed in the following table.

The kinase inhibitors may target AXL (Tyrosine-protein kinase receptor UFO, also known as AXL oncogene; UniprotKB—P30530). The AXL kinase inhibitors are well-known. For instance, reviews are published disclosing such AXL kinase inhibitors (Myers et al, J Med Chem. 2016 Apr. 28; 59(8):3593-608; Grullich, Recent Results Cancer Res. 2018; 211:67-75), the disclosure of which being incorporated herein by reference. Patent applications also disclose AXL kinase inhibitors, for instance and non-exhaustively WO18121228, WO17059280, WO17028797, WO16166250, WO16104617, WO16097918, WO16006706, WO15143692, WO15119122, WO15100117, WO15068767, WO15017607, WO15012298, WO13115280, WO13074633, WO12135800, WO12028332, WO10090764, WO10083465, WO10005876, WO10005879, WO09127417, WO09054864, WO08128072, WO08098139, WO08083353, WO08083357, WO08083354, WO08083356, WO08083367, WO08080134, WO08045978, WO07030680, the disclosure of which being incorporated herein by reference. Specific examples of AXL kinase inhibitors are disclosed in the following table.

The kinase inhibitors may target c-KIT (Mast/stem cell growth factor receptor Kit, also known as Piebald trait protein (PBT), Proto-oncogene c-Kit, Tyrosine-protein kinase Kit or p145 c-kit; UniprotKB—P10721). The c-KIT kinase inhibitors are well-known. For instance, reviews are published disclosing such c-KIT kinase inhibitors (Abbaspour Babaei et al, Drug Des Devel Ther. 2016 Aug. 1; 10:2443-59, Zschabitz et GrWllich; Recent Results Cancer Res. 2018; 211:187-198; Miyamoto et al, Jpn J Clin Oncol. 2018 Jun. 1; 48(6):503-513; Chen et al, Curr Top Med Chem. 2017 Nov. 20; 17(28):3099-3130; Gallogly et Lazarus, J Blood Med. 2016 Apr. 19; 7:73-83; Pitoia et Jerkovich, Drug Des Devel Ther. 2016 Mar. 11; 10:1119-31, Chen et Chen, Drug Des Devel Ther. 2015 Feb. 9; 9:773-9), the disclosure of which being incorporated herein by reference. Patent applications also disclose c-KIT kinase inhibitors, for instance and non-exhaustively WO19034128, WO18112136, WO18112140, WO17167182, WO17121444, WO14202763, WO13033116, WO13033203, WO13033167, WO13033070, WO13014170, WO09105712, WO08011080, WO08005877, WO07124369, WO07092403, WO07038669, WO07026251, WO06106437, WO06135719, WO06060381, WO05073225, WO05021531, WO05021537, WO05021544, WO04080462, WO04014903, WO03035049, WO03002114, WO03003006, WO03004006, the disclosure of which being incorporated herein by reference. Specific examples of c-KIT kinase inhibitors are disclosed in the following table.

The kinase inhibitors may target Trk (Tropomyosin receptor kinase, also known as high affinity nerve growth factor receptor, neurotrophic tyrosine kinase receptor, or TRK-transforming tyrosine kinase protein; UniprotKB—P04629 (Trk1), Q16620 (Trk2), Q16288 (Trk3)). The Trk kinase inhibitors are well-known. For instance, reviews are published disclosing such Trk kinase inhibitors (Bhangoo et Sigal, Curr Oncol Rep. 2019 Feb. 4; 21(2):14, Pacenta et Macy, Drug Des Devel Ther. 2018 Oct. 23; 12:3549-3561; Cocco et al, Nat Rev Clin Oncol. 2018 December; 15(12): 731-747; Lange et Lo, Cancers (Basel). 2018 Apr. 4; 10(4); Rolfo et al, Expert Opin Investig Drugs. 2015; 24(11):1493-500), the disclosure of which being incorporated herein by reference. Patent applications also disclose Trk kinase inhibitors, for instance and non-exhaustively WO18199166, WO18079759, WO17135399, WO17087778, WO17006953, WO16164286, WO16161572, WO16116900, WO16036796, WO16021629, WO15200341, WO15175788, WO15143653, WO15148350, WO15148344, WO15143654, WO15148373, WO15148354, WO15143652, WO15089139, WO15039334, WO15042085, WO15039333, WO15017533, WO14129431, WO14105958, WO14078417, WO14078408, WO14078378, WO14078372, WO14078331, WO14078328, WO14078325, WO14078322, WO14078323, WO13183578, WO13176970, WO13161919, WO13088257, WO13088256, WO13009582, WO12158413, WO12137089 WO12116217, WO12034091, WO12037155, WO11006074, WO10048314, WO10033941, WO09054468, WO08135785, WO07123269, WO06135719, WO06123113, WO06087538, WO06087530, WO06082392, WO05049033, WO03027111, the disclosure of which being incorporated herein by reference. Specific examples of Trk kinase inhibitors are disclosed in the following table.

The kinase inhibitors may target ROS1 (Proto-oncogene tyrosine-protein kinase ROS, also known as Proto-oncogene c-Ros, Proto-oncogene c-Ros-1, Receptor tyrosine kinase c-ros oncogene 1 and c-Ros receptor tyrosine kinase; UniprotKB—P08922). The ROS1 kinase inhibitors are well-known. For instance, reviews are published disclosing such ROS1 kinase inhibitors (Lin et Shaw, J Thorac Oncol. 2017 November; 12(11):1611-1625; Facchinetti et al, Cancer Treat Rev. 2017 April; 55:83-95; Rolfo et al, Expert Opin Investig Drugs. 2015; 24(11):1493-500, Yang et Gong, Expert Rev Clin Pharmacol. 2019 March; 12(3):173-178, Liu et al, Ther Clin Risk Manag. 2018 Jul. 20; 14:1247-1252; Sgambato et al, Expert Rev Anticancer Ther. 2018 January; 18(1):71-80), the disclosure of which being incorporated herein by reference. Patent applications also disclose ROS1 kinase inhibitors, for instance and non-exhaustively WO13183578, WO13180183, WO13158859, WO12037155, WO12005299, WO14141129, WO15144801, WO15144799, WO18170381, the disclosure of which being incorporated herein by reference. Specific examples of ROS1 kinase inhibitors are disclosed in the following table.

The kinase inhibitors may target BTK (Tyrosine-protein kinase BTK, also known as Agammaglobulinemia tyrosine kinase (ATK), B-cell progenitor kinase (BPK) and Bruton tyrosine kinase; UniprotKB—Q06187). The BTK kinase inhibitors are well-known. For instance, reviews are published disclosing such BTK kinase inhibitors (Kim H O, Arch Pharm Res. 2019 February; 42(2):171-181; Liang et al, Eur J Med Chem. 2018 May 10; 151:315-326, Aw et Brown, Drugs Aging. 2017 July; 34(7):509-527; Wu et al, Oncotarget. 2017 Jan. 24; 8(4):7201-7207, Wu et al, J Hematol Oncol. 2016 Sep. 2; 9(1):80), the disclosure of which being incorporated herein by reference. Patent applications also disclose BTK kinase inhibitors, for instance and non-exhaustively WO18002958, WO18001331, WO18009017, WO18035080, WO18088780, WO18090792, WO18095398, WO18133151, WO18145525, A1WO18154131, WO18175512, A1WO18192536, WO18192532, WO18196757, WO18208132, WO18233655, WO19034009, WO17007987, WO17046604, WO17066014, WO17077507, WO17123695, WO17127371, WO17128917, WO17190048, WO17106429, WO16019233, WO16057500, WO16065222, WO16066726, WO16106628, WO16106626, WO16106629, WO16109215, WO16106627, WO16106623, WO16106624, WO16106652, WO16112637, WO16161571, WO16161570, WO16196776, WO16196840, WO16192074, WO16210165, WO16109220, WO15017502, WO15002894, WO15022926, WO15048689, WO15048662, WO15061247, WO15084998, WO15095102, WO15095099, WO15116485, WO15169233, WO15165279, WO15132799, WO15039612, WO14104757, WO14113932, WO14114185, WO14113942, WO14116504, WO14130693, WO14164558, WO14151620, WO14152114, WO14161799, WO14187319, WO14210255, WO14005217, WO14025976, WO14039899, WO14055928, WO14055934, WO14068527, WO14078578, WO14082598, WO14082598, WO13067264, WO13081016, WO13102059, WO13116382, WO13148603, WO13152135, WO13185084, WO13067277, WO13067274, WO13059738, WO13010869, WO13010380, WO13010868, WO12170976, WO12135801, WO12021444, WO11153514, WO11152351, WO11029043, WO11029046, WO10126960, WO10056875, WO10009342, WO09156284, WO09098144, WO09053269, WO08121742, WO08039218, WO9954286, the disclosure of which being incorporated herein by reference. Specific examples of BTK kinase inhibitors are disclosed in the following table.

The kinase inhibitors may target Syk (Tyrosine-protein kinase SYK, also known as Spleen tyrosine kinase, p72-Syk; UniprotKB—P43405). The Syk kinase inhibitors are well-known. For instance, reviews are published disclosing such Syk kinase inhibitors (Bartaula-Brevik et al, Expert Opin Investig Drugs. 2018 April; 27(4):377-387; Liu et Mamorska-Dyga, J Hematol Oncol. 2017; 10: 145, Geahlen, Trends Pharmacol Sci. 2014 August; 35(8):414-22; Norman Expert Opin Ther Pat. 2014 May; 24(5):573-95), the disclosure of which being incorporated herein by reference. Patent applications also disclose Syk kinase inhibitors, for instance and non-exhaustively WO19034153, WO18053189, WO18053190, WO18108083, WO18228475, WO17046302, WO16010809, WO15138273, WO15140051, WO15140054, WO15140055, WO15144614, WO15017610, WO15061369, WO15094997, WO15095444, WO15095445, WO15100217, WO14051654, WO14048065, WO14060371, WO14064134, WO14074422, WO14086032, WO14093191, WO14100314, WO14176210, WO14176216, WO14023385, WO14027300, WO14031438, WO14029732, WO14045029, WO13192125, WO13192128, WO13192098, WO13192088, WO13047813, WO13052391, WO13052394, WO13052393, WO13064445, WO13099041, WO13104573, WO13104575, WO13109882, WO13124026, WO13126132, WO13124025, WO12002577 WO12025187 WO12025186, WO12061418, WO12123311, WO12123312, WO12130780, WO12151137, WO12154519, WO12154520, WO12154518, WO12167423, WO12167733, WO11086085, WO11014795, WO11014515, WO11075515, WO11075560, WO11079051, WO11092128, WO11112995, WO11117160, WO11134971, WO11144584, WO11144585, WO10068257, WO10068258, WO10097248, WO10147898, WO09131687, WO09136995, WO09145856, WO09031011, WO08033798, WO07129226, WO07042298, WO07042299, WO307028445, WO07009681, WO07009681, WO07085540, WO06093247, WO05033316, WO05026158, WO03063794, WO03057695, WO01183485, WO0147922, WO0109134, WO0075113, the disclosure of which being incorporated herein by reference. Specific examples of Syk kinase inhibitors are disclosed in the following table.

In a very specific aspect, the kinase inhibitor can be selected in the following table:

| Target | Type | Drug |
|---|---|---|
| EGFR | Tyrosine | gefitinib, erlotinib, lapatinib, vandetanib, afatinib, osimertinib, neratinib, dacomitinib, brigatinib, canertinib, naquotinib, nazartinib, pelitinib, rociletinib, icotinib, AZD3759, AZ5104, poziotinib, WZ4002 |
| ALK | Tyrosine | Crizotinib, entrectinib, ceritinib, alectinib, brigatinib, lorlatinib, TSR-011, CEP-37440, ensartinib |
| B-Raf | Serine/threonine | Vemurafenib, dabrafenib, regorafenib, PLX4720 |
| MEK1/2 | Dual specificity | Cobimetinib, Trametinib, Binimetinib, Selumetinib, PD-325901, CI-1040, PD035901, U0126, TAK-733 |
| FGFR family including FGFR1, FGFR2, FGFR3 and FGFR4 | Tyrosine | Lenvatinib (FGFR1/2/3/4); Debio-1347 and dovitinib (FGFR 1/2/3); BLU9931 (FGFR4); regorafenib |
| FLT3 | Tyrosine | Sorafenib, sunitinib, lestaurtinib, tandutinib, quizartinib, crenolanib, gilteritinib, ponatinib, ibrutinib |
| IGF1R | Tyrosine | Linsitinib, NVP-AEW541, BMS-536924, AG-1024, GSK1838705A, BMS-754807, PQ 401, ZD3463, NT157, Picropodophyllin (PPP) |
| c-Met | Tyrosine | Tivantinib, JNJ-38877605, PF-04217903, foretinib (GSK 1363089), Merestinib |
| JAK | Tyrosine | Ruxolitinib, tofacitinib, oclacitinib, baricitinib, filgotinib, cerdulatinib, gandotinib, lestaurtinib, momelotinib, pacritinib, PF-04965842, upadacitinib, peficitinib, fedratinib |

-continued

| Target | Type | Drug |
|---|---|---|
| PDGFR α/β | Tyrosine | imatinib, regorafenib, sunitinib, sorafenib, pazopanib, Telatinib, bosutinib, nilotinib, ponatinib, lenvatinib |
| RET | Tyrosine | cabozantinib, vandetanib, lenvatinib |
| AXL | Tyrosine | Bemcentinib, amuvatinib, bosutinib, cabozantinib, foretinib, gilteritinib (ASP2215), glesatinib (MGCD 265), SGI-7079 |
| TrkA, TrkB, TrkC | Tyrosine | Larotrectinib, entrectinib, RXDX-102, altiratinib, LOXO-195, sitravatinib |
| ROS1 | Tyrosine | crizotinib, entrectinib, lorlatinib, ceritinib, cabozantinib, TPX-0005, DS-6051b |
| BTK | Tyrosine | Ibrutinib, Acalabrutinib, GS-4059, spebrutinib, BGB-3111, HM7122 |
| Syk | Tyrosine | fostamatinib, entospletinib, cerdulatinib, TAK-659 |

In some embodiments, the kinase inhibitor is an EGFR inhibitor. For instance, it can be selected from the group consisting of gefitinib, erlotinib, lapatinib, vandetanib, afatinib, osimertinib, neratinib, dacomitinib, brigatinib, canertinib, naquotinib, nazartinib, pelitinib, rociletinib, and icotinib.

In some embodiments, the subject suffers from a cancer showing an increased activation of the MAPK pathway (i.e. "cancer associated with activation of the MAPK pathway"). As used herein, increased expression or activity is understood as an expression level or activity level which is at least 10%, at least 20%, at least 30%, at least 40%, at least 500%, at least 100%, at least 200%, at least 300% or more with respect to a reference expression level or to a reference activity level. Methods for determining whether the expression level of a given component of the MAPK pathway is increased are well-known in the art and include methods based on the determination of the mRNA levels of the corresponding component (e.g., Northern blot, RT-PCR and the like) and methods based on the determination of the protein levels of the corresponding component (e.g., ELISA, Western blot, etc.). Methods for determining whether the activity of one or more components of the MAPK pathway is increased are based on the determination of the activity of the different components and are widely known to the skilled person. Suitable methods for determining the activity of the MAPK pathway include, for instance, the detection of phosphorylated ERK (MAPK) protein as well as the ratio of phosphoERK to ERK.

In some embodiments, the subject suffers from a cancer characterized by the presence of least one mutation in a protein involved in the MAPK pathway. Typically, the cancer is characterized by at least one mutation in a tyrosine kinase receptor (e.g. FGFR1, FGFR2, FGFR3, EGFR, HER2, IGF-1R cMET . . . ), BRAF, RAS, CRAF, CCND1, CDK4, MAP2K1, MAP2K2, NRAS, KRAS HRAS, PTEN, PIK3CA, and P16.

In some embodiments, the subject suffers from an EGFR-mutated cancer. As used herein, the term "EGFR" has its general meaning in the art and refers to the Epidermal Growth Factor Receptor. EGFR is s a well-known transmembrane protein that is a receptor for members of the epidermal growth factor family (EGF family) of extracellular protein ligands. The epidermal growth factor receptor is a member of the ErbB family of receptors, a subfamily of four closely related receptor tyrosine kinases: EGFR (ErbB-1), HER2/neu (ErbB-2), Her 3 (ErbB-3) and Her 4 (ErbB-4). As used herein, the expression "EGFR-mutated cancer" refers to a cancer in which the cancer cells comprise an activating mutation in EGFR. A number of mutations in EGFR are known and typically include L858R, T790M, and C797S.

In some embodiments, the subject suffers from an ALK-mutated cancer. As used herein, the term "ALK" has its general meaning in the art and refers to anaplastic lymphoma kinase (ALK), that is involved in cell growth. Mutated (changed) forms of the ALK gene and protein have been found in some types of cancer, including neuroblastoma, non-small cell lung cancer, and anaplastic large cell lymphoma. These changes may increase the growth of cancer cells. As used herein, the expression "ALK-mutated cancer" refers to a cancer in which the cancer cells comprise an activating mutation in ALK. A number of mutations in ALK are known. ALK mutations are well known and there are three types of ALK mutations: rearrangement (ALK-R), amplification (ALK-A), and point mutation. Several point mutations conferring drug resistance have been identified, including: C1156Y, L1196M, G1269A, F1174L, 1151Tins, L1152R, S1206Y, 11171T, G1202, D1203N, and V1180L.

In some embodiments, the subject suffers from a RAS-mutated cancer. As used herein, the term "RAS" represents any member of the RAS family of proteins or mutants thereof. Ras family proteins include, but are not limited to, HRAS, KRAS and NRAS, as well as other members of this subfamily as well: DIRAS1; DIRAS2; DIRAS3; ERAS; GEM; MRAS; NKIRAS1; NKIRAS2; NRAS; RALA; RALB; RAPlA; RAP1B; RAP2A; RAP2B; RAP2C; RASD1; RASD2; RASL10A; RASLIOB; RASLI1A; RASL11B; RASL12; REM1; REM2; RERG; RERGL; RRAD; RRAS; RRAS2 (Wennerberg et al., The Ras superfamily at a glance, J. Cell. Sci., 2005, 118 (Pt 5), 843-846). Accordingly, the expression "mutated-RAS cancer" refers to a cancer in which the cancer cells comprise an activating mutation in a Ras protein. In particular, the subject suffers from a NRAS-mutated cancer. A number of mutations in NRAS are known and typically include Q61R, Q61K, Q61H, Q61L, Q61N, Q61E, Q61P, A146T, A146P, or A146V.

In some embodiments, the subject suffers from a RAF-mutated cancer. As used herein, the term "RAF" represents any member of the Raf family of proteins or mutants thereof. RAFfamily proteins include, but are not limited to A-RAF, B-RAF and C-RAF. Accordingly, the expression "mutated-RAF cancer" refers to a cancer in which the cancer cells comprise an activating mutation in a Raf protein. In particular, the subject suffers from a BRAF-mutated cancer. A number of mutations in BRAF are known. In particular, the V600E mutation is prominent. Other mutations which have been found are R4611, 1462S, G463E, G463V, G465A, G465E, G465V, G468A, G468E, N580S, E585K, D593V, F594L, G595R, L596V, T5981, V599D, V599E, V599K, V599R, V600E, A727V, and most of these mutations are clustered to two regions: the glycine-rich P loop of the N lobe and the activation segment and flanking regions. As is known in the art, several PCR and/or sequencing based methods are known for use in detecting mutations in the MAPK pathway and are presented in several research articles and US patents including, but not limited to, Brose, et al. Cancer Research 62:6997-7000 (2002), Solit et al, Cancer Research 70(14): 5901-5911 (1010), Xu, et al. Cancer research 63:4561-4567 (2003), as well as U.S. Pat. No. 7,745,128, and several commercially available kits (see Dxs Diagnostic Innovations, Applied Biosystems, and Quest diagnostics Various cancers are also encompassed by the scope of the invention, including, but not limited to, the following: carcinoma including that of the bladder (including accelerated and metastatic bladder cancer), breast, colon (including colorectal cancer), kidney, liver, lung (including small and non-small cell lung cancer and lung adenocarcinoma), ovary, prostate, testis, genitourinary tract, lymphatic system, rectum, larynx, pancreas (including exocrine pancreatic carcinoma), esophagus, stomach, gall bladder, cervix, thyroid, and skin (including squamous cell carcinoma); hematopoietic tumors of lymphoid lineage including leukemia, acute lymphocytic leukemia, acute lymphoblastic leukemia, B-cell lymphoma, T-cell lymphoma (including cutaneous or peripheral T-cell lymphoma), Hodgkins lymphoma, non-Hodgkins lymphoma, hairy cell lymphoma, histiocytic lymphoma, and Burketts lymphoma; hematopoietic tumors of myeloid lineage including acute and chronic myelogenous leukemias, myelodysplastic syndrome, myeloid leukemia, and promyelocytic leukemia; tumors of the central and peripheral nervous system including astrocytoma, neuroblastoma, glioma, and schwannomas; tumors of mesenchymal origin including fibrosarcoma, rhabdomyosarcoma, and osteosarcoma; other tumors including melanoma, xenoderma pigmentosum, keratoactanthoma, seminoma, thyroid follicular cancer, and teratocarcinoma; melanoma, unresectable stage III or IV malignant melanoma, squamous cell carcinoma, small-cell lung cancer, non-small cell lung cancer, glioma, gastrointestinal cancer, renal cancer, ovarian cancer, liver cancer, colorectal cancer, endometrial cancer, kidney cancer, prostate cancer, thyroid cancer, neuroblastoma, pancreatic cancer, glioblastoma multiforme, cervical cancer, stomach cancer, bladder cancer, hepatocarcinoma, breast cancer, colon carcinoma, and head and neck cancer, retinoblastoma, gastric cancer, germ cell tumor, bone cancer, bone tumors, adult malignant fibrous histiocytoma of bone; childhood malignant fibrous histiocytoma of bone, sarcoma, pediatric sarcoma; myelodysplastic syndromes; neuroblastoma; testicular germ cell tumor, intraocular melanoma, myelodysplastic syndromes; myelodysplastic/myeloproliferative diseases, synovial sarcoma.

In some embodiments, the cancer is a solid tumor. For instance, the cancer may be sarcoma and osteosarcoma such as Kaposi sarcome, AIDS-related Kaposi sarcoma, melanoma, in particular uveal melanoma, and cancers of the head and neck, kidney, ovary, pancreas, prostate, thyroid, lung, esophagus, breast in particular triple negative breast cancer (TNBC), bladder, colorectum, liver and biliary tract, uterine, appendix, and cervix, testicular cancer, gastrointestinal cancers and endometrial and peritoneal cancers. Preferably, the cancer may be sarcoma, melanoma, in particular uveal melanoma, and cancers of the head and neck, kidney, ovary, pancreas, prostate, thyroid, lung, esophagus, breast in particular (TNBC), bladder, colorectum, liver, cervix, and endometrial and peritoneal cancers.

In some embodiments, the cancer can be selected from the group consisting of leukemia, lymphoma, sarcoma, melanoma, and cancers of the head and neck, kidney, ovary, pancreas, prostate, thyroid, lung, esophagus, breast, bladder, brain, colorectum, liver, and cervix.

In some embodiments, the cancer can be selected from the group consisting of lung cancer, in particular non-small cell lung cancer, leukemia, in particular acute myeloid leukemia, chronic lymphocytic leukemia, lymphoma, in particular peripheral T-cell lymphoma, chronic myelogenous leukemia, squamous cell carcinoma of the head and neck, advanced melanoma with BRAF mutation, colorectal cancer, gastrointestinal stromal tumor, breast cancer, in particular $HER2^+$ breast cancer, thyroid cancer, in particular advanced medullary thyroid cancer, kidney cancer, in particular renal cell carcinoma, prostate cancer, glioma, pancreatic cancer, in particular pancreatic neuroendocrine cancer, multiple myeloma, and liver cancer, in particular hepatocellular carcinoma.

In particular, the subject suffers from a lung cancer. As used herein, the term "lung cancer" has its general meaning in the art and refers to a disease in tissues of the lung involving uncontrolled cell growth, which, in some cases, leads to metastasis. The majority of primary lung cancers are carcinomas of the lung, derived from epithelial cells. The main types of lung cancer are small cell lung carcinoma (SCLC) and non-small cell lung carcinoma (NSCLC). In a particular embodiment, the subject suffers from a non-small cell lung cancer. As used herein, the term "non-small cell lung cancer," also known as non-small cell lung carcinoma (NSCLC), refers to epithelial lung cancer other than small cell lung carcinoma (SCLC). There are three main subtypes: adenocarcinoma, squamous cell lung carcinoma, and large cell lung carcinoma. Other less common types of non-small cell lung cancer include pleomorphic, carcinoid tumor, salivary gland carcinoma, and unclassified carcinoma. Adenocarcinomas account for approximately 40% of lung cancers, and are the most common type of lung cancer in people who have never smoked. Squamous cell carcinomas account for about 25% of lung cancers. Squamous cell carcinoma of the lung is more common in men than in women and is even more highly correlated with a history of tobacco smoking than are other types of lung carcinoma. There are at least four variants (papillary, small cell, clear cell, and basaloid) of squamous cell carcinoma of the lung. Large cell lung carcinomas are a heterogeneous group of malignant neoplasms originating from transformed epithelial cells in the lung. Large cell lung carcinomas are carcinomas that lack light microscopic characteristics of small cell carcinoma, squamous cell carcinoma, or adenocarcinoma. NSCLC may be categorized using the tumor-nodes-metastasis (TNM) staging system. See Spira J & Ettinger, D. S. Multidisciplinary management of lung cancer, N Engl J Med, 350:382-(2004) (hereinafter Spira); Greene F L, Page D L, Fleming I D, Fritz A G, Balch C M, Haller D G, et al (eds). AJCC Cancer Staging Manual. 6th edition. New York: Springer-Verlag, 2002:167-77 (hereinafter Greene); Sobin L H, Wittekind C H (eds). International Union Against Cancer. TNM classification of malignant tumours. 6th edition. New York: Wiley-Liss (2002) (hereinafter Sobin). Accordingly, in some embodiments, the lung cancer may be stratified into any of the preceding stages (e.g., occult, stage 0, stage IA, stage IB, stage IIA, stage IIB, stage IIIA, stage IIIB or stage IV). More particularly, the subject suffers from a EGFR-mutated NSCLC or an ALK-mutated NSLC as described above.

In particular, the subject suffers from melanoma, in particular metastatic melanoma. As used herein, "melanoma" refers to a condition characterized by the growth of a tumor arising from the melanocytic system of the skin and other organs. Most melanocytes occur in the skin, but are also found in the meninges, digestive tract, lymph nodes and eyes. When melanoma occurs in the skin, it is referred to as cutaneous melanoma. Melanoma can also occur in the eyes and is called ocular or intraocular melanoma. Melanoma occurs rarely in the meninges, the digestive tract, lymph nodes or other areas where melanocytes are found. 40-60% of melanomas carry an activating mutation BRAF.

In some embodiments, if the kinase inhibitor is an EGFR inhibitor, the cancer is preferably selected from the group consisting of lung cancer, in particular non-small cell lung cancer, pancreatic cancer, breast cancer, in particular early breast cancer, thyroid cancer, in particular medullary thyroid cancer, colorectal cancer, in particular metastatic or advanced colorectal cancer, squamous cell carcinoma of the head and neck and glioma. If the kinase inhibitor is an ALK inhibitor, the cancer is preferably non-small cell lung cancer. If the kinase inhibitor is a B-Raf inhibitor, the cancer is preferably selected from the group consisting of melanoma, lung cancer, colorectal cancer and gastro-intestinal stromal cancer. If the kinase inhibitor is an MEK inhibitor, the cancer is preferably melanoma or lung cancer. If the kinase inhibitor is a FGFR inhibitor, the cancer is preferably selected from the group consisting of thyroid carcinoma, colorectal cancer and gastro-intestinal stromal cancer. If the kinase inhibitor is a FLT3 inhibitor, the cancer is preferably selected from the group consisting of kidney cancer, pancreatic cancer, especially pancreatic neuroendocrine tumor, gastro-intestinal stromal cancer, multiple myeloma, prostate cancer, leukemia such as acute myeloid leukemia and chronic lymphocytic leukemia, and lymphoma. If the kinase inhibitor is a JAK inhibitor, the cancer is preferably selected from the group consisting of lymphoma, especially peripheral T-cell lymphoma, myeloproliferative neoplasms, multiple myeloma, pancreatic cancer, and prostate cancer. If the kinase inhibitor is a PDGFR inhibitor, the cancer is preferably selected from the group consisting of leukemia such as Philadelphia chromosome-positive chronic myeloid leukemia, gastro-intestinal stromal cancer, myelodysplastic and myeloproliferative syndromes, colorectal cancer, kidney cancer, pancreatic cancer, in particular pancreatic neuroendocrine tumor, liver cancer, breast cancer, and thyroid carcinoma. If the kinase inhibitor is a RET inhibitor, the cancer is preferably kidney cancer or thyroid cancer such as medullary thyroid cancer. If the kinase inhibitor is an AXL inhibitor, the cancer is preferably selected from the group consisting of leukemia, in particular acute leukemia such as acute myeloid leukemia or Philadelphia chromosome-positive chronic myeloid leukemia, kidney cancer, and lung cancer such as NSCLC. If the kinase inhibitor is a Trk inhibitor, the cancer is preferably a metastatic solid cancer. If the kinase inhibitor is a ROS1 inhibitor, the cancer is preferably selected from the group consisting of lung cancer such as NSCLC and kidney cancer. If the kinase inhibitor is a BTK inhibitor, the cancer is preferably selected from the group consisting of B cell cancers such as chronic lymphocytic leukemia (CLL) and non-Hodgkin lymphoma. If the kinase inhibitor is a Syk inhibitor, the cancer is preferably lymphoma, especially peripheral T-cell lymphoma.

As used herein, the term "farnesyltransferase inhibitor" may be understood in the broadest sense as a molecule that prevents the enzymatically catalysed transfer of a farnesyl residue to a substrate. Herein, the substrate that is farnesylated is typically a polypeptide of at least four amino acids in length. A polypeptide that is enzymatically catalysed famesylysed preferably includes a CAAX-sequence-motive, at which C represents a cysteine moiety, A an aliphatic amino acid moiety and X another amino acid moiety that is identified by the enzyme that catalyses the farnesylation. As used herein, the enzymatically catalysed transfer of a farnesyl residue describes a biochemical reaction in which a famesyl residue is transferred to a substrate, preferably a polypeptide. An enzyme that catalyses the transfer of a farnesyl residue to a substrate is called famesyltransferase. In this case, typically, activated farnesole is transferred. Activated famesole is preferably famesyldiphosphate (farnesylpyrophosphate, FPP). Typically, the polypeptide that represents the substrate is farnesylated to a cysteine moiety. So a thiolester is generated. The terms "thiolester" and "thioester" are exchangeable and describe a R1—CO—S—R2 group, wherein a thiolester can also comprise the tautomeric form of the ester R1—COH═S—R2. Preferably, the cysteine moiety that may be farnesylated is localised near to the C-terminal ending of the protein. Particularly preferably, the cysteine moiety of a CAAX-sequence-motive is farnesylated, wherein C represents a cysteine moiety, A an aliphatic amino acid moiety and X another amino acid moiety that is identified by the enzyme that catalyses the farnesylation.

The enzyme that catalyses the farnesylation is preferably a famesyltransferase (FTase), that represents a prenyltransferase with the enzyme-classification-number EC 2.5.1.X, more preferably EC 2.5.1.29, EC 2.5.1.58 or EC 2.5.1.59, even more preferably EC 2.5.1.29 or EC 2.5.1.58. The enzyme typically binds one or several zinc ion(s) ($Zn^{2+}$). Geranylgeranyltransferase may also be effective as farnesyltransferase in the sense of the invention, because this enzyme is also able to famesylate particular polypeptides.

Every substance or every molecular composition that is able to decelerate or to prevent the enzymatically catalysed farnesylation may be a famesyltransferase inhibitor. Preferably, a deceleration of the farnesylation rate may be understood as a deceleration of more than 10%, more preferred of more than 25%, even more preferred of more than 50%, even more preferred of more than 75%, even more preferred of more than 80%, even more preferred of more than 90% and most preferred of more than 95% by the addition of the farnesyltransferase inhibitor in an suitable concentration at the site of action compared to a similar reaction environment without addition of the famesyltransferase inhibitor.

More importantly, the farnesyltransferase inhibitor inhibits the farnesylation of RhoB. As used herein, the term "Rho B" has its general meaning in the art and refers to ras homolog gene family, member B that is a protein which in humans is encoded by the RHOB gene.

In some embodiments, the farnesyltransferase inhibitor may be an antimetabolite such as, exemplarily, an analogue of farnesole, farnesylphosphate, famesyldiphosphate or a substrate peptide. The famesyltransferase inhibitor may also be a molecule with a different structure that may bind into the binding pocket of the peptide substrate or the famesyldiphosphate. Alternatively, the farnesyltransferase inhibitor may be an allosteric inhibitor.

In some embodiments, the famesyltransferase inhibitor may have any molecular structure. For example, it may be a peptidic agent, a peptidomimetic or a non-peptidic small-molecular agent. A peptidic agent mostly consists of a peptide. However, the peptide may be conjugated to other molecular structures such as, exemplarily, to an organic, biologically compatible polymer (e.g., polyethylene glycol (PEG), polyethylenimine (PEI), hydroxypropyl methacrylamide (HPMA), to a lipid, an alkyl moiety or to another polypeptide. A peptidomimetic is an agent which molecular structure mimics a peptide. A peptidomimetic may contain, for example, beta-amino acids (1 amino acids), gamma-amino acids (y amino acids) or D-amino acids or it may be made out of these or out of a combination of several thereof. A peptidomimetic may also be conjugated to other molecular structures such as, exemplarily, an organic biologically compatible polymer. A peptidomimetic may also be a retro-inverse peptide. A small molecule agent is a molecule with a molecular weight of less than 1500 Da, preferably less than 1000 Da, even more preferably less than 500 Da. A small molecule agent may also be conjugated to other molecular structures such as, exemplarily, an organic biologically compatible polymer.

In some embodiments, the famesyltransferase inhibitor is selected from the group consisting of R11577 (Zamestra, Tipifamib), SCH66336 (Lonafamib), FTI-277, GGTI-298, BMS-214664, L-778 and L-123.

In some embodiments, the famesyltransferase inhibitor of the present invention is Tipifarnib. As used herein, the term "tipifarnib", also known under the trade name Zarnestra® (J&JPRD), refers to an FTase inhibitor (R)-6-[amino(4-chlorophenyl)(1-methyl-1H-imidazol-5-yl)methyl]-4-(3-chlorophenyl)-1-methyl-2(1H)-quinolinone (also identified as R1 15777) having the structure shown below:

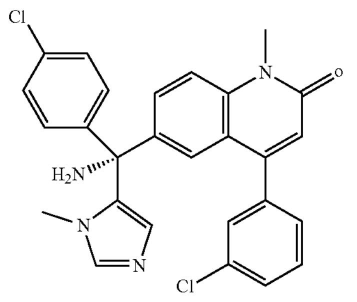

As used herein, the term "combination" is intended to refer to all forms of administration that provide a first drug together with a further (second, third . . . ) drug. The drugs may be administered simultaneous, separate or sequential and in any order. Drugs administered in combination have biological activity in the subject to which the drugs are delivered. Within the context of the invention, a combination thus comprises at least two different drugs, and wherein one drug is at least a kinase inhibitor and wherein the other drug is a farnesyltransferase inhibitor. In some instance, the combination of the present invention results in the synthetic lethality of the cancer cells, in particular DTC.

A "therapeutically effective amount" refers to an amount effective, at dosages and for periods of time necessary, to achieve a desired therapeutic result. A therapeutically effective amount of drug may vary according to factors such as the disease state, age, sex, and weight of the individual, and the ability of drug to elicit a desired response in the individual. A therapeutically effective amount is also one in which any toxic or detrimental effects of the antibody or antibody portion are outweighed by the therapeutically beneficial effects. The efficient dosages and dosage regimens for drug depend on the disease or condition to be treated and may be determined by the persons skilled in the art. A physician having ordinary skill in the art may readily determine and prescribe the effective amount of the pharmaceutical composition required. For example, the physician could start doses of drug employed in the pharmaceutical composition at levels lower than that required in order to achieve the desired therapeutic effect and gradually increase the dosage until the desired effect is achieved. In general, a suitable dose of a composition of the present invention will be that amount of the compound which is the lowest dose effective to produce a therapeutic effect according to a particular dosage regimen. Such an effective dose will generally depend upon the factors described above. For example, a therapeutically effective amount for therapeutic use may be measured by its ability to stabilize the progression of disease. A therapeutically effective amount of a therapeutic compound may decrease tumor size, or otherwise ameliorate symptoms in a subject. One of ordinary skill in the art would be able to determine such amounts based on such factors as the subject's size, the severity of the subject's symptoms, and the particular composition or route of administration selected. An exemplary, non-limiting range for a therapeutically effective amount of drug is about 0.1-100 mg/kg, such as about 0.1-50 mg/kg, for example about 0.1-20 mg/kg, such as about 0.1-10 mg/kg, for instance about 0.5, about such as 0.3, about 1, about 3 mg/kg, about 5 mg/kg or about 8 mg/kg. An exemplary, non-limiting range for a therapeutically effective amount of an antibody of the present invention is 0.02-100 mg/kg, such as about 0.02-30 mg/kg, such as about 0.05-10 mg/kg or 0.1-3 mg/kg, for example about 0.5-2 mg/kg. Administration may e.g. be intravenous, intramuscular, intraperitoneal, or subcutaneous, and for instance administered proximal to the site of the target. Dosage regimens in the above methods of treatment and uses are adjusted to provide the optimum desired response (e.g., a therapeutic response). For example, a single bolus may be administered, several divided doses may be administered over time or the dose may be proportionally reduced or increased as indicated by the exigencies of the therapeutic situation. In some embodiments, the efficacy of the treatment is monitored during the therapy, e.g. at predefined points in time. As non-limiting examples, treatment according to the present invention may be provided as a daily dosage of the agent of the present invention in an amount of about 0.1-100 mg/kg, such as 0.2, 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of days 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of weeks 1, 2, 3, 4, 5, 6, 7, 8, 9, 10, 11, 12, 13, 14, 15, 16, 17, 18, 19 or 20 after initiation of treatment, or any combination thereof, using single or divided doses every 24, 12, 8, 6, 4, or 2 hours, or any combination thereof.

Typically, the drug of the present invention is administered to the subject in the form of a pharmaceutical composition which comprises a pharmaceutically acceptable carrier. Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. For use in administration to a subject, the composition will be formulated for administration to the subject. The compositions of the present invention may be administered orally, parenterally, by inhalation spray, topically, rectally, nasally, buccally, vaginally or via an implanted reservoir. The used herein includes subcutaneous, intravenous, intramuscular, intra-articular, intra-synovial, intrasternal, intrathecal, intrahepatic, intralesional and intracranial injection or infusion techniques. Sterile injectable forms of the compositions of this invention may be aqueous or an oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation. The compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include, e.g., lactose. When aqueous suspensions are required for oral use, the active ingredient is combined with emulsifying and suspending agents. If desired, certain sweetening, flavoring or coloring agents may also be added. Alternatively, the compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols. The compositions of this invention may also be administered topically, especially when the target of treatment includes areas or organs readily accessible by topical application, including diseases of the eye, the skin, or the lower intestinal tract. Suitable topical formulations are readily prepared for each of these areas or organs. For topical applications, the compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water. Topical application for the lower intestinal tract can be effected in a rectal suppository formulation (see above) or in a suitable enema formulation. Patches may also be used. The compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents. For example, an antibody present in a pharmaceutical composition of this invention can be supplied at a concentration of 10 mg/mL in either 100 mg (10 mL) or 500 mg (50 mL) single-use vials. The product is formulated for IV administration in 9.0 mg/mL sodium chloride, 7.35 mg/mL sodium citrate dihydrate, 0.7 mg/mL polysorbate 80, and Sterile Water for Injection. The pH is adjusted to 6.5. An exemplary suitable dosage range for an antibody in a pharmaceutical composition of this invention may between about 1 $mg/m^2$ and 500 $mg/m^2$. However, it will be appreciated that these schedules are exemplary and that an optimal schedule and regimen can be adapted taking into account the affinity and tolerability of the particular antibody in the pharmaceutical composition that must be determined in clinical trials. A pharmaceutical composition of the invention for injection (e.g., intramuscular, i.v.) could be prepared to contain sterile buffered water (e.g. 1 ml for intramuscular), and between about 1 ng to about 100 mg, e.g. about 50 ng to about 30 mg or more preferably, about 5 mg to about 25 mg, of the inhibitor of the invention.

A further object of the present invention relates to a pharmaceutical composition or a kit (kit-of-parts) comprising a Farnesyltransferase inhibitor and a kinase inhibitor, in particular for use for treating cancer.

The terms "kit", "product" or "combined preparation", as used herein, defines especially a "kit-of-parts" in the sense that the combination partners as defined above can be dosed independently or by use of different fixed combinations with distinguished amounts of the combination partners, i.e. simultaneously or at different time points. The parts of the kit-of-parts can then, e.g., be administered simultaneously or chronologically staggered, that is at different time points and with equal or different time intervals for any part of the kit of parts. The ratio of the total amounts of the combination partners to be administered in the combined preparation can be varied. The combination partners can be administered by the same route or by different routes.

The invention will be further illustrated by the following figures and examples. However, these examples and figures should not be interpreted in any way as limiting the scope of the present invention.

FIGURES

Figure 1C:
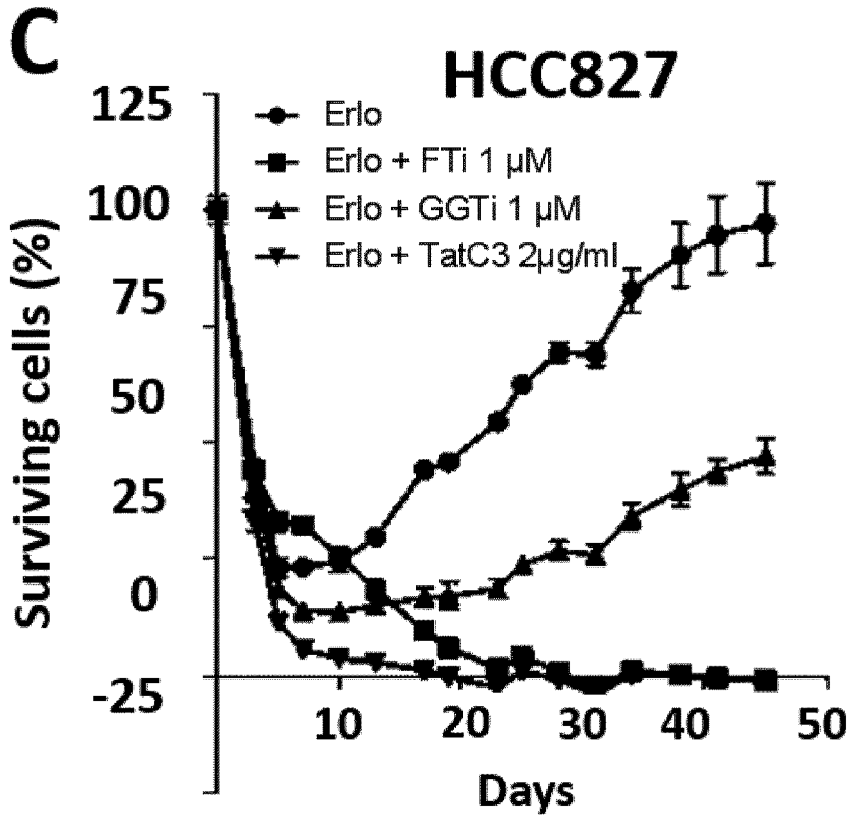
Figure 1D:
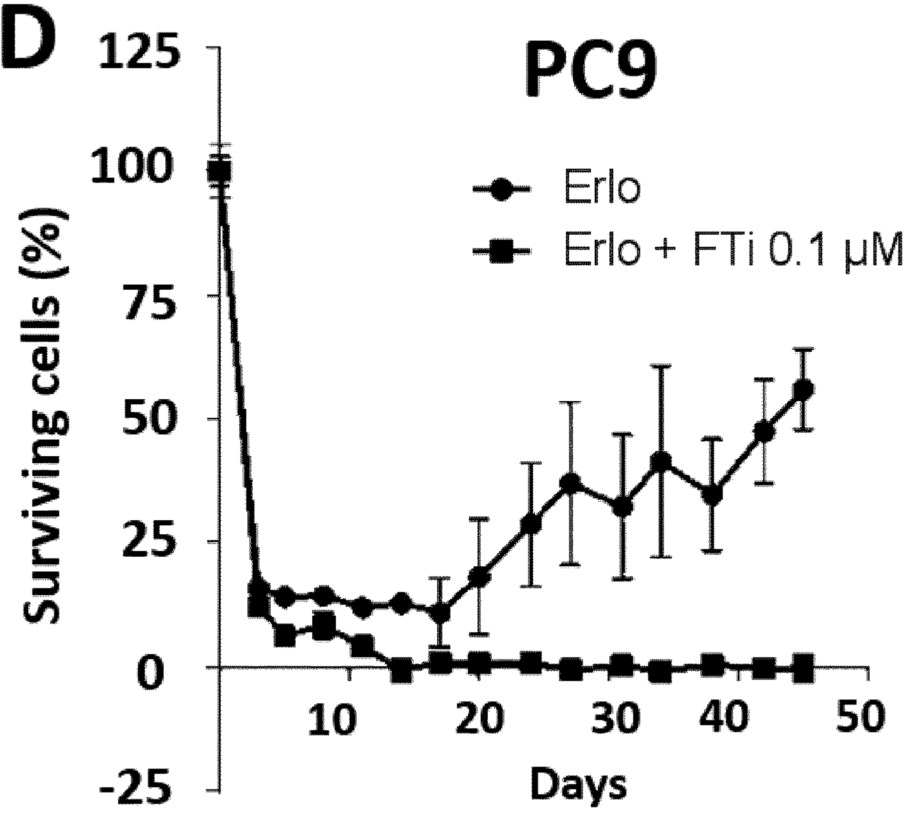
Figures 1E, 1F:
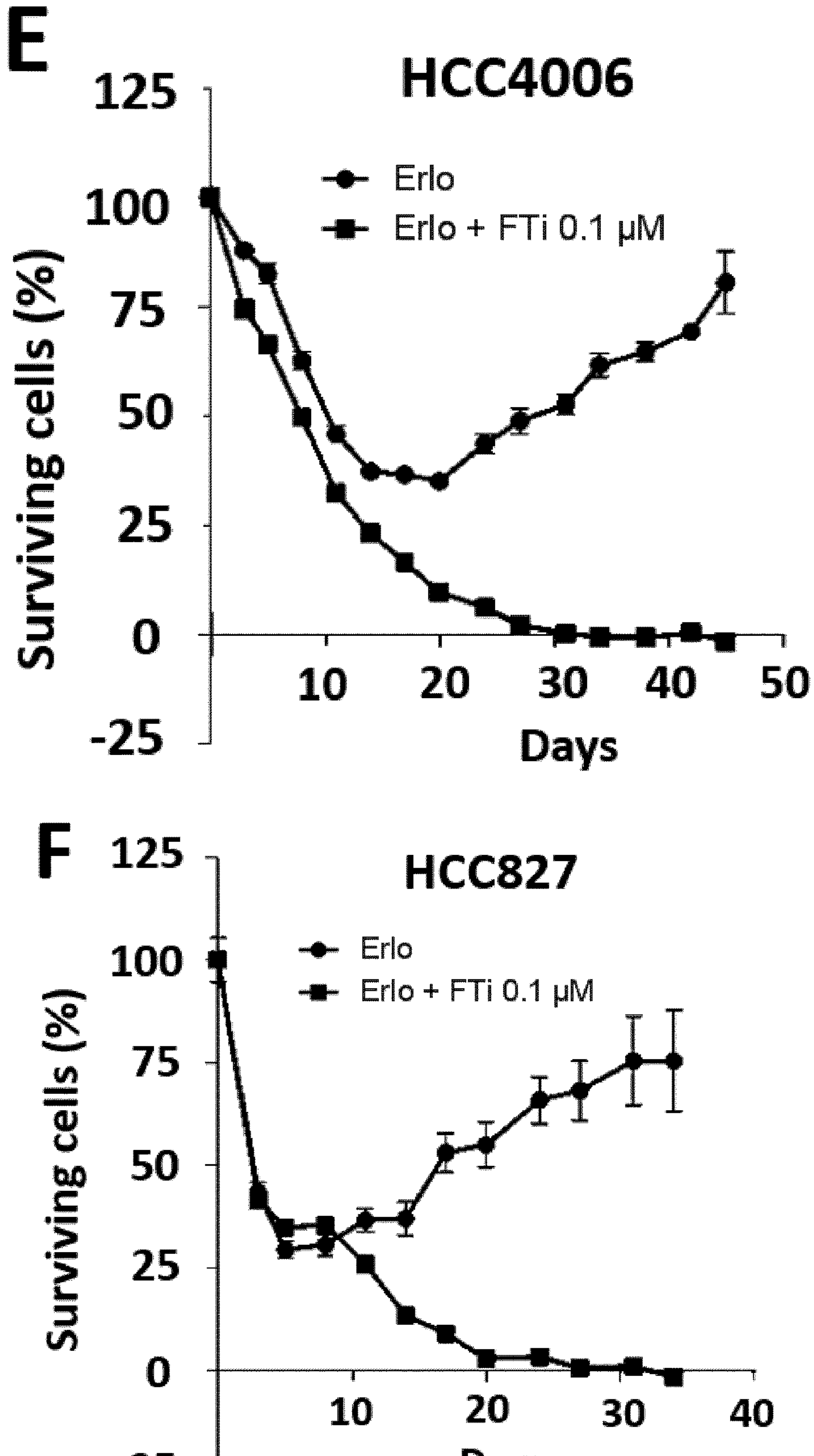
Figure 1G:
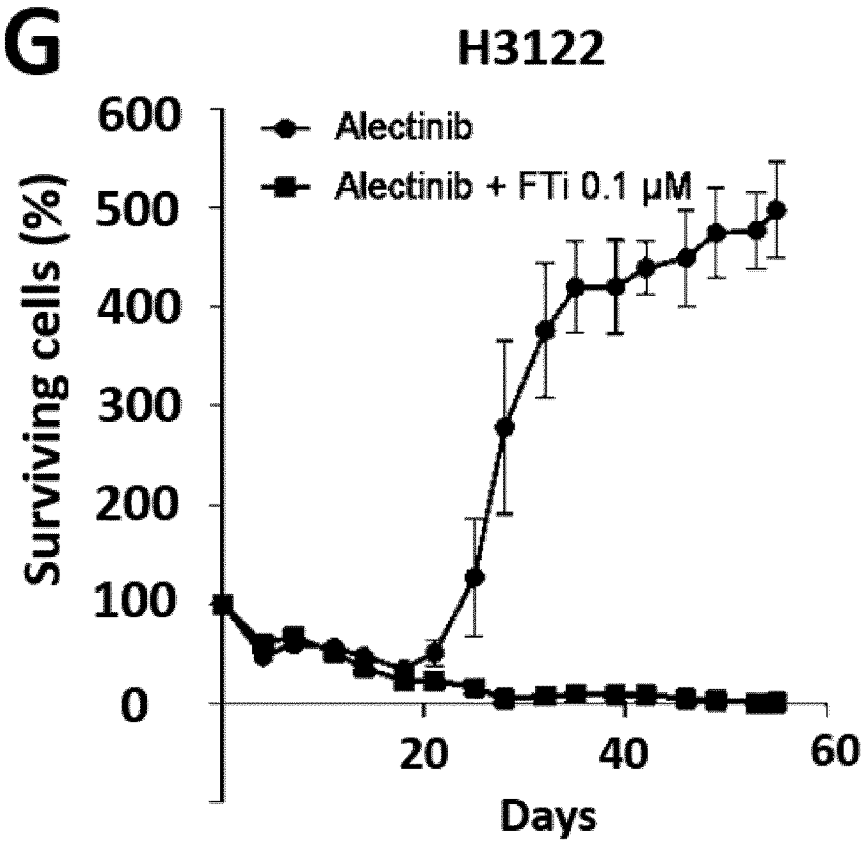
Figure 1H:
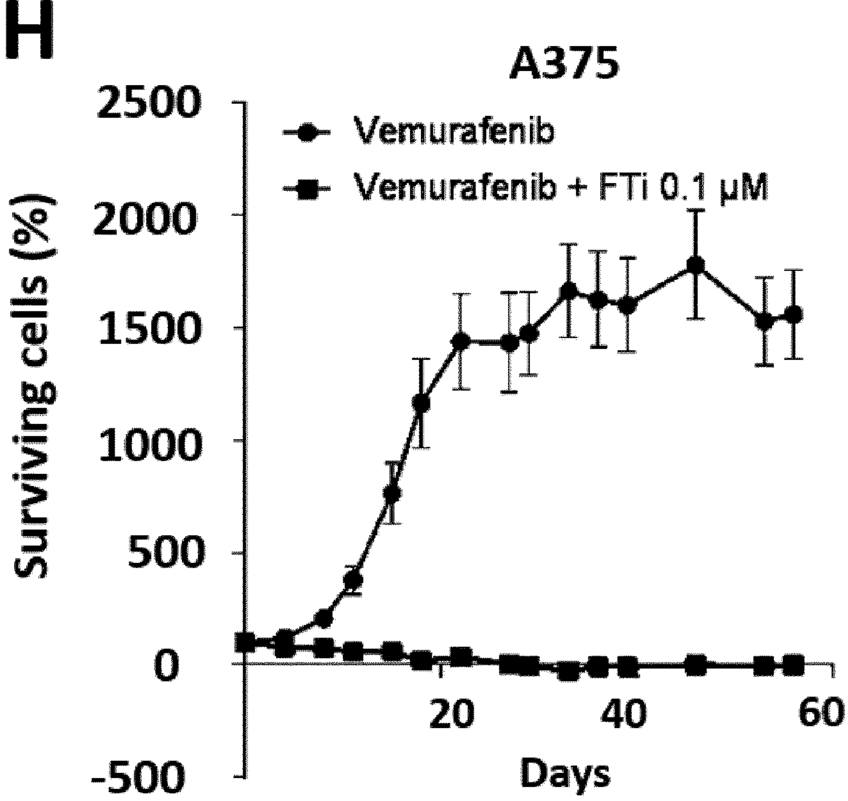

FIG. 1. FTi but not GGTi prevent relapse in several TKI-sensitive models. GFP-transduced EGFR-mutated cell lines were treated with Erlotinib at 1 μM with or without FTi (Tipifarnib, 1 μM), GGTi (GGTi-298, 1 μM) or TatC3 (2 μg/ml) (A-C), or Tipifarnib at 0.1 μM (D-F), and response as well as relapse was followed by fluorescence detection. (G-H). GFP-transduced H3122 (ALK-translocated NSCLC cell line) or A375 (BRAF-mutated melanoma cell line) were treated by Tipifarnib 0.1 μM in combination with Alectinib (2 μM) or Vemurafenib (5 μM), respectively, and response as well as relapse was followed by fluorescence detection.

Figure 2A:
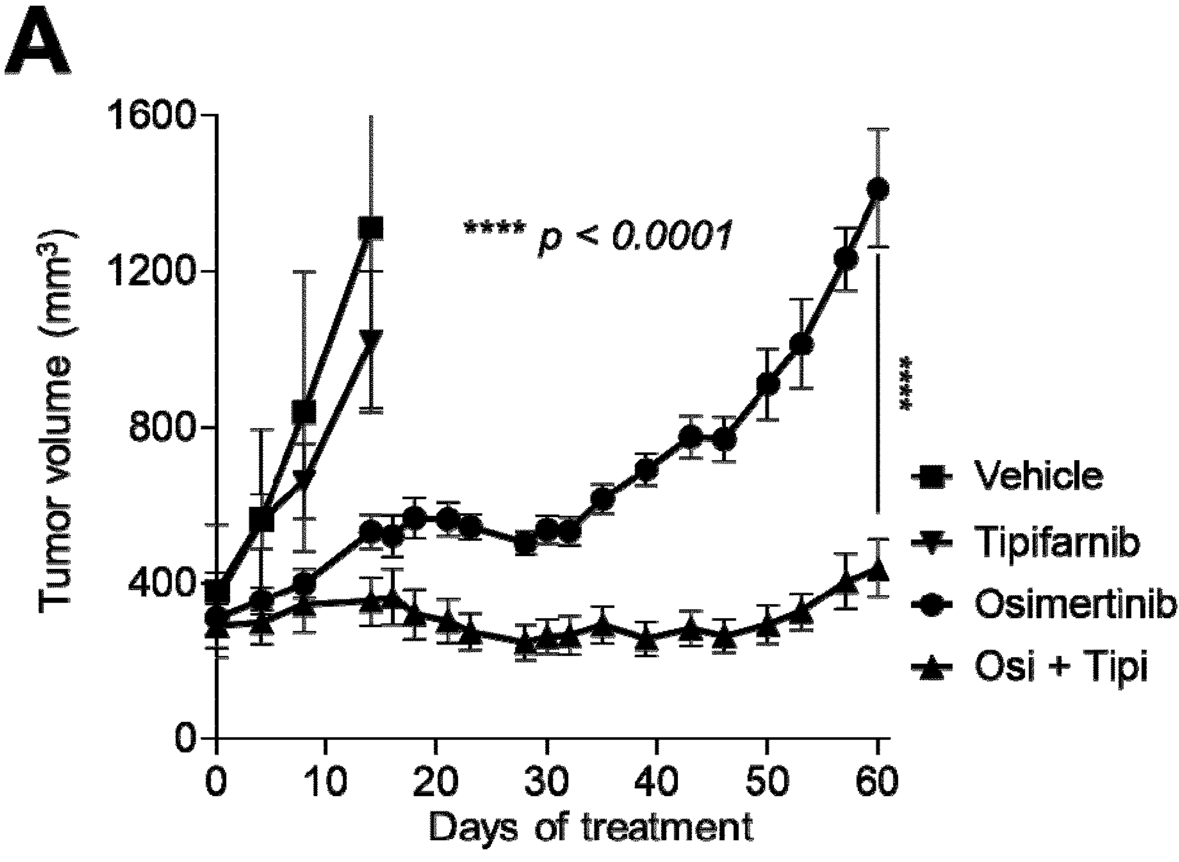
Figure 2B:
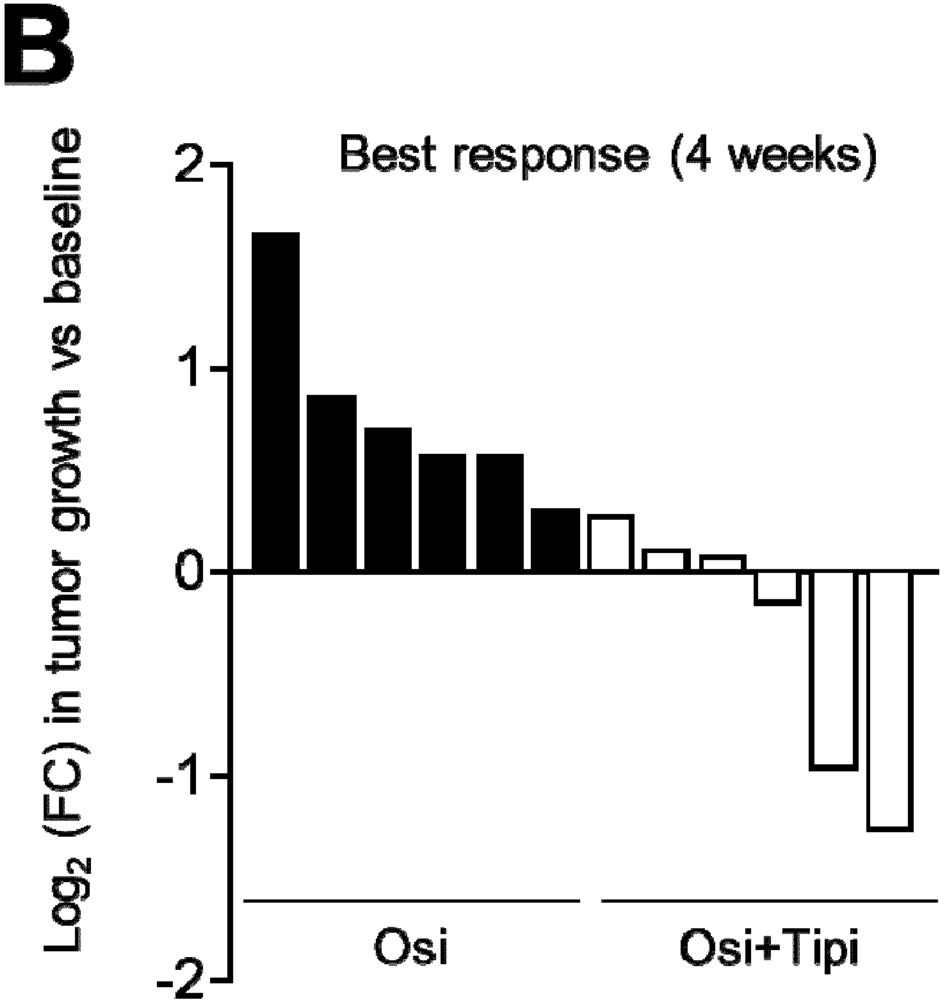
Figure 2C:
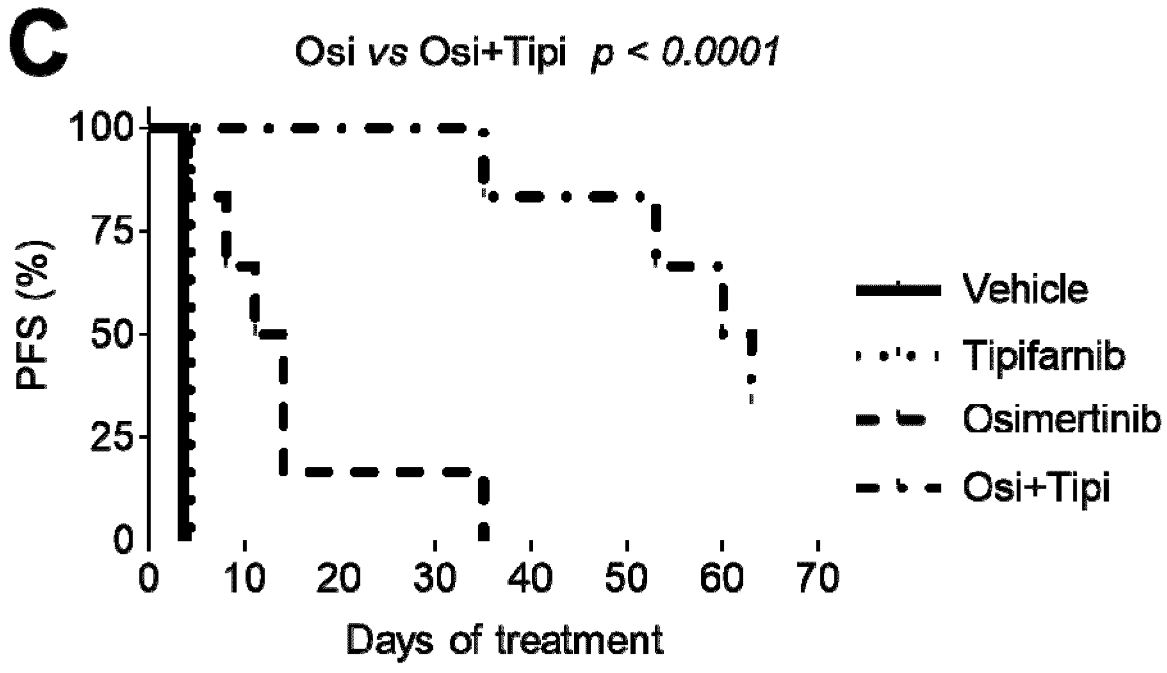
Figure 2D:
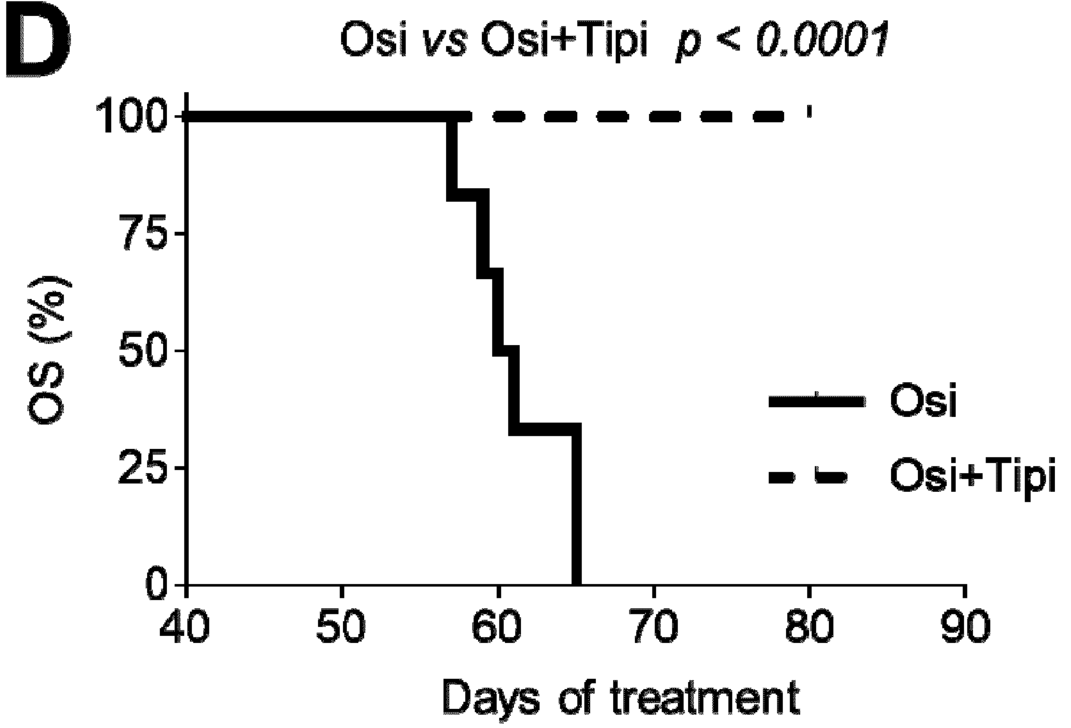
Figure 2E:
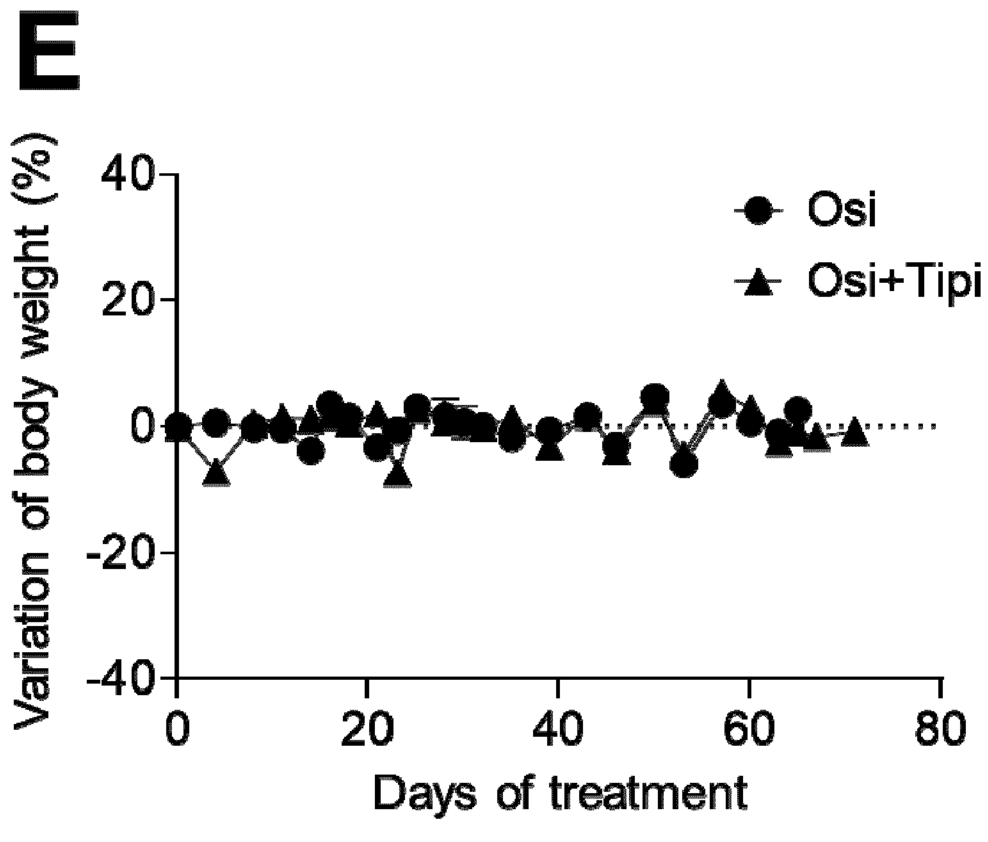

FIG. 2. (A) Evolution of tumor volume upon indicated treatments. (B) Evolution of tumor size vs baseline at best response (45 days). (C) Kaplan-Meier progression-free survival plot. (D) Kaplan-Meier overall survival plot. (E) Evolution of mice body size during treatment.

EXAMPLE

In Vitro:

We recently reported that the RAS-related GTPase RHOB has a pivotal role in preventing cell death through the AKT pathway in EGFR-mutated lung cancer cells treated with EGFR-TKI[18]. We found that high RHOB tumor levels predict the early relapse of NSCLC patients harbouring EGFR-activating mutations treated with EGFR-TKI. This was also true in BRAF-mutated melanomas treated with the BRAF inhibitor vemurafenib[19], suggesting that the RHOB pathway could be a common adaptive mechanism to receptor tyrosine kinase (RTK)-ERK pathway inhibition that might induce the acquisition of a DTC state. We have also identified a new phenotype related to drug tolerance in vitro after EGFR-TKI treatment that shares several characteristics of a known process of Therapy-Induced Senescence (TIS)[20] but also displays some specific features (data not shown). We will thus refer this phenotype to as "senescent-like". These observations arise from an extensive phenotypic characterization of the DTC state in a panel of EGFR-mutated lung cell lines (that were previously cloned to avoid the presence of potential resistant sub-clones in the bulk population) including the well described PC9 but also HCC827, HCC4006, H3255, and HCC2935 which all display initial sensitivity to EGFR-TKI but have not been yet characterized for their ability to produce DTC in response to EGFR-TKI. Surprisingly, although all these cell lines were able to generate DTC after several days of EGFR-TKI treatment (erlotinib or osimertinib at 1 μM), we observed a high variability intra- and inter-cell lines for several critical parameters such as cell division rate/cell arrest or kinetics of proliferative clones' onset. For instance, PC9, HCC827 and HCC4006 were able to generate proliferative resistant clones after erlotinib treatment, but we never observed resistant clones after erlotinib treatment in HCC2935 and H3255 cell lines (data not shown).

Despite these differences, we also observed that a common feature of the DTC state among the cell lines was a cell shape reorganization during treatment, mainly a flattened and enlarged morphology, consistent with a TIS process (data not shown). We further explore these morphological changes and we observed a strong increase in actin stress fibers production a few days after initiation of TKI treatment (data not shown). Actin polymerization is a tightly regulated process orchestrated by GTPases. Given our knowledge on the role of RHOB in resistance to targeted therapy, we assessed whether this GTPase could be responsible for the production of stress fibers in response to EGFR-TKI. We first observed that RHOB protein expression and activity were highly increased in DTC in all cell lines, whereas RHOA and RHOC were strongly inhibited (data not shown). We also found that siRNA-specific inhibition of RHOB as well as pharmacological inhibition of RHO-GTPases using C3 exoenzyme (tatC3) not only strongly decreased the production of actin stress fibers but also strongly decreased DTC survival, suggesting a link between actin remodelling and drug-tolerance (data not shown).

RHOB has no clinically-compatible specific inhibitor, however its activity is dependent on its prenylation status (either farnesylated or geranylgeranylated) and thus can be targeted by famesyltransferase inhibitors (FTi) or geranylgeranyl transferase inhibitors (GGTi)[21-23]. Therefore, we decided to determine in vitro the efficacy of FTi or GGTi in combination with erlotinib in several EGFR-mutated cell lines (PC9, HCC827 and HCC4006). Combination with GGTI 298 at 1 μM didn't prevent the emergence of resistant proliferative clones (FIGS. 1A-C), whereas combination with FTi Tipifarnib efficiently eliminated all drug tolerant cells when used at 1 μM (FIGS. 1A-C) but also at 0.1 μM (FIGS. 1D-F), and fully prevented the emergence of resistant clones. Interestingly, similar results were observed in other oncogenic models such as ALK-translocated lung cancer cells (e.g. H3122) treated with Alectinib (FIG. 1G) or BRAF-mutated melanoma cells (A375) treated with Vemurafenib (FIG. 1H), suggesting that co-treatment with Tipifarnib could interfere with other targeted therapies that target (RTK)-ERK pathway.

Tipifarnib used alone at 0.1 μM showed little-to-non effect on PC9 and HCC827 cells growth (data not shown), but showed some cytostatic effect on HCC4006 (data not shown), A375 and H3122, that was exacerbated when Tipifarnib was used at 1 μM (data not shown). Importantly, combination of Tipifarnib (0.1p m) and Erlotinib (1 μM) resulted in complete cell death revealed by the absence of remaining DTC after several days of treatment (data not shown). Interestingly, same results were observed with third generation EGFR-TKI Osimertinib that will be now used as standard first-line treatment for NSCLC patients harbouring EGFR mutations (data not shown).

Altogether, our in vitro data strongly suggest that Famesyltransferase (but not geranylgeranyl transferase) inhibition can prevent the emergence of resistances to Tyrosine Kinase Inhibitors in different oncogenic contexts. Excitingly, a recently published phase I clinical trial reported that combination of Erlotinib and Tipifarnib was well tolerated in patients[24], however the efficiency of the combination is not indicative since this study was not performed on EGFR-mutated NSCLC patients.

In Vivo

Previously described EGFRL858R/T790M lung Patient Derived Xenograft model (TP103, Pax Ares' lab, CNIO Madrid) was implanted sub-cutaneously in 6-8 week old NSG mice (Charles River) and tumors were allowed to establish, sizes (average 300-350 mm3) were matched and then mice were randomly allocated to the following groups: vehicle (n=3), Tipifarnib (n=3), Osimertinib (n=6) and Osimertinib+Tipifarnib (n=6). Tipifanib was administrated by oral gavage at 80 mg/Kg twice a day, 5 days/week and Osimertinib was administrated by oral gavage at 5 mg/Kg once a day, 5 days/week. Tumor size was determined by caliper measurements of tumor length and width and tumor volume was calculated as volume=0.5236×length×width2 (mm), and the mice were weighed once a week. GraphPad Prism (GraphPad Software) was used to perform unpaired two-tailed t-test or Mantel-Cox for PFS and OS plot (FIGS. 2A to 2E).

REFERENCES

Throughout this application, various references describe the state of the art to which this invention pertains. The disclosures of these references are hereby incorporated by reference into the present disclosure.

1 Fitzmaurice, C. et al. The Global Burden of Cancer 2013. JAMA Oncol 1, 505-527, doi:10.1001/jamaoncol.2015.0735 (2015).
2 Rosell, R. et al. Erlotinib versus standard chemotherapy as first-line treatment for European patients with advanced EGFR mutation-positive non-small-cell lung cancer (EURTAC): a multicentre, open-label, randomised phase 3 trial. Lancet Oncol 13, 239-246, doi:10.1016/S1470-2045(11)70393-X (2012).
3 Engelman, J. A. et al. MET amplification leads to gefitinib resistance in lung cancer by activating ERBB3 signaling. Science 316, 1039-1043, doi:10.1126/science.1141478 (2007).
4 Takezawa, K. et al. HER2 amplification: a potential mechanism of acquired resistance to EGFR inhibition in EGFR-mutant lung cancers that lack the second-site EGFRT790M mutation. Cancer discovery 2, 922-933, doi:10.1158/2159-8290.CD-12-0108 (2012).
5 Thomson, S. et al. Epithelial to mesenchymal transition is a determinant of sensitivity of non-small-cell lung carcinoma cell lines and xenografts to epidermal growth factor receptor inhibition. Cancer research 65, 9455-9462, doi:10.1158/0008-5472.CAN-05-1058 (2005).
6 Yu, H. A. et al. Analysis of tumor specimens at the time of acquired resistance to EGFR-TKI therapy in 155 patients with EGFR-mutant lung cancers. Clinical cancer research: an official journal of the American Association for Cancer Research 19, 2240-2247, doi:10.1158/1078-0432.CCR-12-2246 (2013).
7 Calvayrac, O., Pradines, A., Pons, E., Mazieres, J. & Guibert, N. Molecular biomarkers for lung adenocarcinoma. The European respiratory journal 49, doi:10.1183/13993003.01734-2016 (2017).
8 Sequist, L. V. et al. Genotypic and histological evolution of lung cancers acquiring resistance to EGFR inhibitors. Sci Transl Med 3,75ra26, doi:10.1126/scitranslmed.3002003 (2011).
9 Niederst, M. J. & Engelman, J. A. Bypass mechanisms of resistance to receptor tyrosine kinase inhibition in lung cancer. Sci Signal 6, re6, doi:10.1126/scisignal.2004652 (2013).
10 Thress, K. S. et al. Acquired EGFR C797S mutation mediates resistance to AZD9291 in non-small cell lung cancer harboring EGFR T790M. Nature medicine 21, 560-562, doi:10.1038/nm.3854 (2015).
11 Sharma, S. V. et al. A chromatin-mediated reversible drug-tolerant state in cancer cell subpopulations. Cell 141, 69-80, doi:10.1016/j.cell.2010.02.027 (2010).
12 Hata, A. N. et al. Tumor cells can follow distinct evolutionary paths to become resistant to epidermal growth factor receptor inhibition. Nature medicine 22, 262-269, doi:10.1038/nm.4040 (2016).
13 Ramirez, M. et al. Diverse drug-resistance mechanisms can emerge from drug-tolerant cancer persister cells. Nature communications 7, 10690, doi:10.1038/ncomms10690 (2016).
14 Guler, G. D. et al. Repression of Stress-Induced LINE-1 Expression Protects Cancer Cell Subpopulations from Lethal Drug Exposure. Cancer cell 32, 221-237 e213, doi:10.1016/j.ccell.2017.07.002 (2017).
15 Fallahi-Sichani, M. et al. Adaptive resistance of melanoma cells to RAF inhibition via reversible induction of a slowly dividing de-differentiated state. Molecular systems biology 13, 905, doi:10.15252/msb.20166796 (2017).
16 Liau, B. B. et al. Adaptive Chromatin Remodeling Drives Glioblastoma Stem Cell Plasticity and Drug Tolerance. Cell stem cell 20, 233-246 e237, doi:10.1016/j.stem.2016.11.003 (2017).
17 Kesarwani, M. et al. Targeting c-FOS and DUSP1 abrogates intrinsic resistance to tyrosine-kinase inhibitor therapy in BCR-ABL-induced leukemia. Nature medicine 23, 472-482, doi:10.1038/nm.4310 (2017).
18 Calvayrac, O. et al. The RAS-related GTPase RHOB confers resistance to EGFR-tyrosine kinase inhibitors in non-small-cell lung cancer via an AKT-dependent mechanism. EMBO molecular medicine 9, 238-250, doi:10.15252/emmm.201606646 (2017).
19 Delmas, A. et al. The c-Jun/RHOB/AKT pathway confers resistance of BRAF-mutant melanoma cells to MAPK inhibitors. Oncotarget 6, 15250-15264, doi:10.18632/oncotarget.3888 (2015).
20 Ewald, J. A., Desotelle, J. A., Wilding, G. & Jarrard, D. F. Therapy-induced senescence in cancer. Journal of the National Cancer Institute 102, 1536-1546, doi:10.1093/jnci/djg364 (2010).
21 Lebowitz, P. F., Davide, J. P. & Prendergast, G. C. Evidence that famesyltransferase inhibitors suppress Ras transformation by interfering with Rho activity. Mol Cell Biol 15, 6613-6622, doi:10.1128/mcb.15.12.6613 (1995).
22 Chen, Z. et al. Both farnesylated and geranylgeranylated RhoB inhibit malignant transformation and suppress human tumor growth in nude mice. J Biol Chem 275, 17974-17978, doi:10.1074/jbc.C000145200 (2000).
23 Lebowitz, P. F. & Prendergast, G. C. Non-Ras targets of farnesyltransferase inhibitors: focus on Rho. Oncogene 17, 1439-1445, doi:10.1038/sj.onc.1202175 (1998).
24 Jazieh, K. et al. A phase I study of the farnesyltransferase inhibitor Tipifarnib in combination with the epidermal growth factor tyrosine kinase inhibitor Erlotinib in patients with advanced solid tumors. Invest New Drugs 37, 307-314, doi:10.1007/s10637-018-0662-1 (2019).

The invention claimed is:

1. A method of treating non-small-cell lung cancer (NSCLC) in a subject in need thereof, comprising:
administering to the subject a therapeutically effective combination comprising an epidermal growth factor receptor (EGFR) kinase inhibitor and tipifarmib, wherein if the NSCLC is metastatic NSCLC then the EGFR kinase inhibitor is not gefitinib.

2. A method for delaying development of a non-small-cell lung cancer (NSCLC) resistant to an EGFR kinase inhibitor in a subject, comprising:
administering to the subject a therapeutically effective amount of the EGFR kinase inhibitor in combination with tipifarmib, wherein if the NSCLC is metastatic NSCLC then the EGFR kinase inhibitor is not gefitinib.

3. A method of treating resistance to an epidermal growth factor receptor (EGFR) kinase inhibitor in a subject suffering from non-small-cell lung cancer (NSCLC), comprising:
administering to the subject a therapeutically effective amount of tipifarmib, wherein if the NSCLC is metastatic NSCLC then the EGFR kinase inhibitor is not gefitinib.

4. The method of claim 1, wherein the EGFR inhibitor is selected from the group consisting of gefitinib, erlotinib, lapatinib, vandetanib, afatinib, osimertinib, neratinib, dacomitinib, brigatinib, canertinib, naquotinib, nazartinib, pelitinib, rociletinib, icotinib, AZD3759, AZ5104 (CAS No 1421373-98-9), poziotinib and WZ4002.

5. The method of claim 1, wherein the subject suffers from an EGFR-mutated cancer.

6. The method of claim 1, wherein the EGFR kinase inhibitor is osimertinib.

7. The method of claim 1, wherein the NSCLC is EGFR-mutated NSCLC and the EGFR kinase inhibitor is osimertinib.

8. The method of claim 2, wherein the NSCLC is EGFR-mutated NSCLC and the EGFR kinase inhibitor is osimertinib.

9. The method of claim 3, wherein the NSCLC is EGFR-mutated NSCLC and the EGFR kinase inhibitor is osimertinib.

10. The method of claim 1, wherein the EGFR kinase inhibitor and tipifarmib are administered simultaneously.

11. The method of claim 1, wherein the EGFR kinase inhibitor and tipifarmib are administered sequentially.

* * * * *